United States Patent
Liu et al.

(10) Patent No.: US 12,403,376 B2
(45) Date of Patent: Sep. 2, 2025

(54) WEARABLE DEVICE AND ACTIVITY DATA COLLECTION METHOD

(71) Applicant: Huawei Technologies Co., Ltd., Shenzhen (CN)

(72) Inventors: Jiangming Liu, Shenzhen (CN); Bo Ke, Shenzhen (CN); Xiaolin Li, Dongguan (CN); De Yang, Shenzhen (CN); Xuejing Feng, Shenzhen (CN); Xia Sun, Nanjing (CN)

(73) Assignee: HUAWEI TECHNOLOGIES CO., LTD., Shenzhen (CN)

(*) Notice: Subject to any disclaimer, the term of this patent is extended or adjusted under 35 U.S.C. 154(b) by 991 days.

(21) Appl. No.: 17/439,229

(22) PCT Filed: Mar. 13, 2020

(86) PCT No.: PCT/CN2020/079150
§ 371 (c)(1),
(2) Date: Sep. 14, 2021

(87) PCT Pub. No.: WO2020/192449
PCT Pub. Date: Oct. 1, 2020

(65) Prior Publication Data
US 2022/0143483 A1 May 12, 2022

(30) Foreign Application Priority Data
Mar. 22, 2019 (CN) .......................... 201910224314.2

(51) Int. Cl.
*G06F 18/24* (2023.01)
*A63B 24/00* (2006.01)
(Continued)

(52) U.S. Cl.
CPC ...... *A63B 71/0622* (2013.01); *A63B 24/0062* (2013.01); *G06F 3/011* (2013.01);
(Continued)

(58) Field of Classification Search
None
See application file for complete search history.

(56) References Cited

U.S. PATENT DOCUMENTS

| | | | |
|---|---|---|---|
| 2014/0197965 A1* | 7/2014 | Park | A61B 5/021 340/870.09 |
| 2015/0005911 A1* | 1/2015 | Lake, II | A63B 71/06 700/91 |

(Continued)

FOREIGN PATENT DOCUMENTS

| | | | |
|---|---|---|---|
| CN | 103399483 A | 11/2013 | |
| CN | 104363987 A | 2/2015 | |

(Continued)

*Primary Examiner* — Scott C Sun
(74) *Attorney, Agent, or Firm* — Conley Rose, P.C.

(57) ABSTRACT

A wearable device, where the wearable device includes at least two working modes. The at least two working modes include a first working mode and a second working mode. The wearable device receives a user operation, the wearable device starts the first working mode in response to a first operation of a user to collect first activity data, where the first activity data is daily activity data of the user, and the wearable device starts the second working mode in response to a second operation of the user to collect second activity data, where the second activity data is professional exercise data of the user.

20 Claims, 18 Drawing Sheets

(51) Int. Cl.
*A63B 71/06* (2006.01)
*G06F 3/01* (2006.01)

(52) U.S. Cl.
CPC ... *A63B 2071/0663* (2013.01); *A63B 2220/20* (2013.01); *A63B 2220/62* (2013.01); *A63B 2220/836* (2013.01); *A63B 2225/50* (2013.01); *A63B 2230/06* (2013.01); *G06F 18/24* (2023.01)

(56) References Cited

U.S. PATENT DOCUMENTS

| | | |
|---|---|---|
| 2015/0065090 A1 | 3/2015 | Yeh |
| 2017/0164851 A1 | 6/2017 | Takahashi |
| 2017/0200014 A1 | 7/2017 | Jing |
| 2017/0359645 A1 | 12/2017 | Chen et al. |
| 2018/0344181 A1 | 12/2018 | Schroeder et al. |

FOREIGN PATENT DOCUMENTS

| | | |
|---|---|---|
| CN | 105392115 A | 3/2016 |
| CN | 106506162 A | 3/2017 |
| CN | 106547829 A | 3/2017 |
| CN | 106851537 A | 6/2017 |
| CN | 107085231 A | 8/2017 |
| CN | 107390860 A | 11/2017 |
| CN | 107580359 A | 1/2018 |
| CN | 109009141 A | 12/2018 |
| CN | 109150220 A | 1/2019 |
| CN | 110134229 A | 8/2019 |
| EP | 3910450 A1 | 11/2021 |
| JP | 2017104382 A | 6/2017 |
| WO | 2009097591 A1 | 8/2009 |

\* cited by examiner

CONT. FROM FIG. 5A

CONT. FROM FIG. 5A

CONT. FROM FIG. 5A

S508: The running activity data →

The user removes the device body 101 from the shoe buckle 103, and fastens the device body 101 to a watchband 102

S509: Display the running activity data on the interface of the app

S510: Detect that the contact voltage is a first voltage value, and determine that the wearable device 100 is in a wristband mode S511: Notify the mobile phone that the wearable device 100 is in the running mode →

S512: The interface of the app prompts the mobile phone that the wearable device 100 is in the wristband mode The user clicks the "Start exercise" button on the interface of the app S513: Receive the click operation performed by the user on the "Start exercise" button on the interface of the app S514: Send the first message in response to the click operation performed by the user on the "Start exercise" button ←

S515: Start a first-type sensor in response to the first message to collect daily activity data S516: The daily activity data →

S517: Display the daily activity data on the interface of the app

FIG. 5B

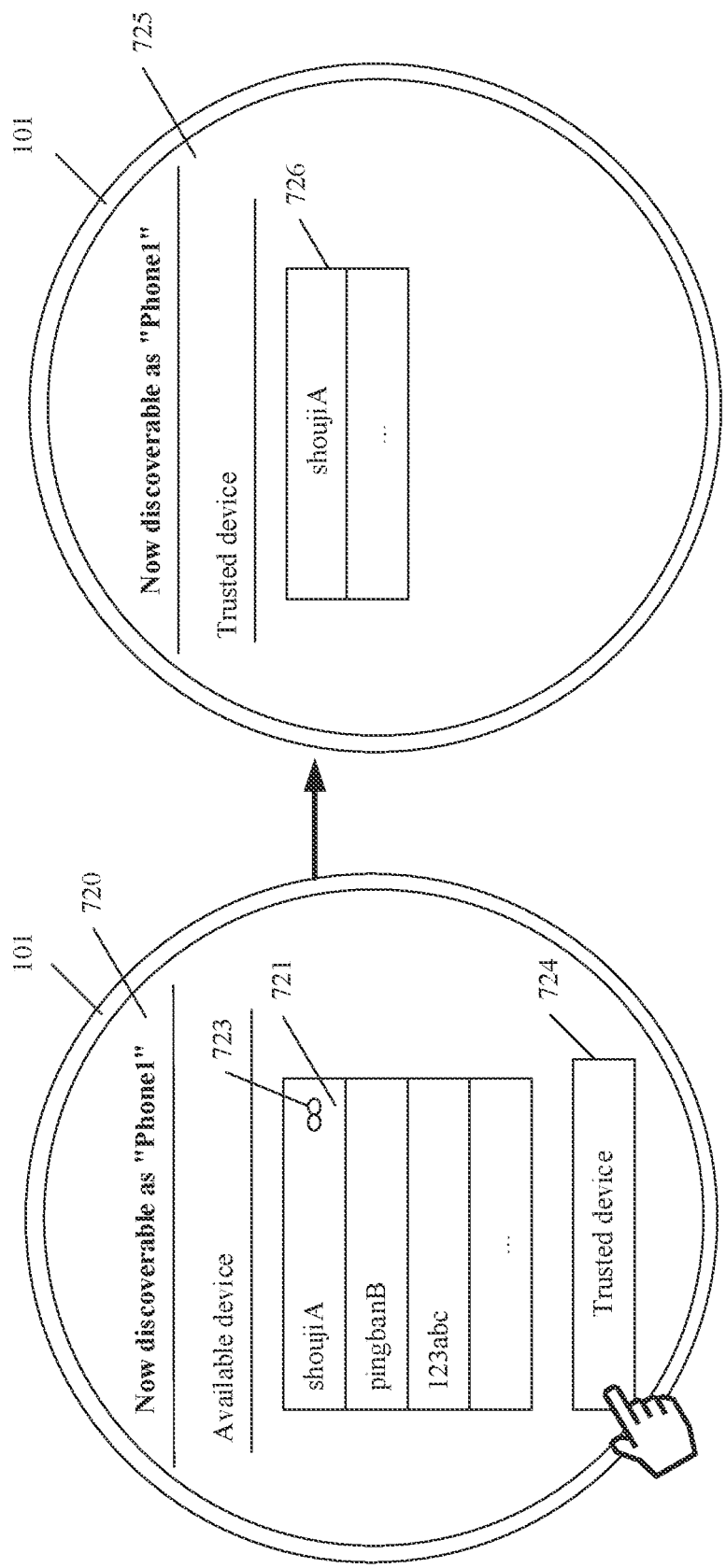

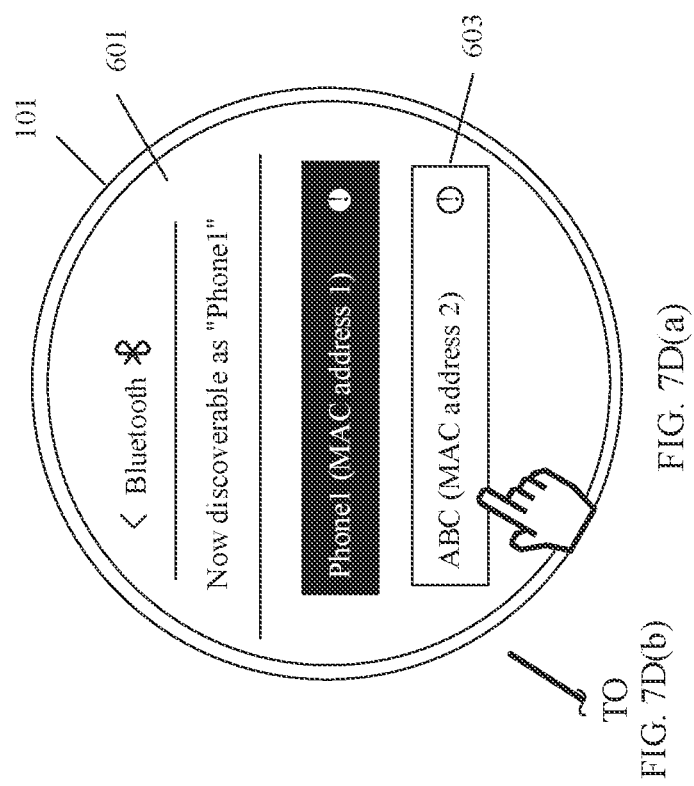

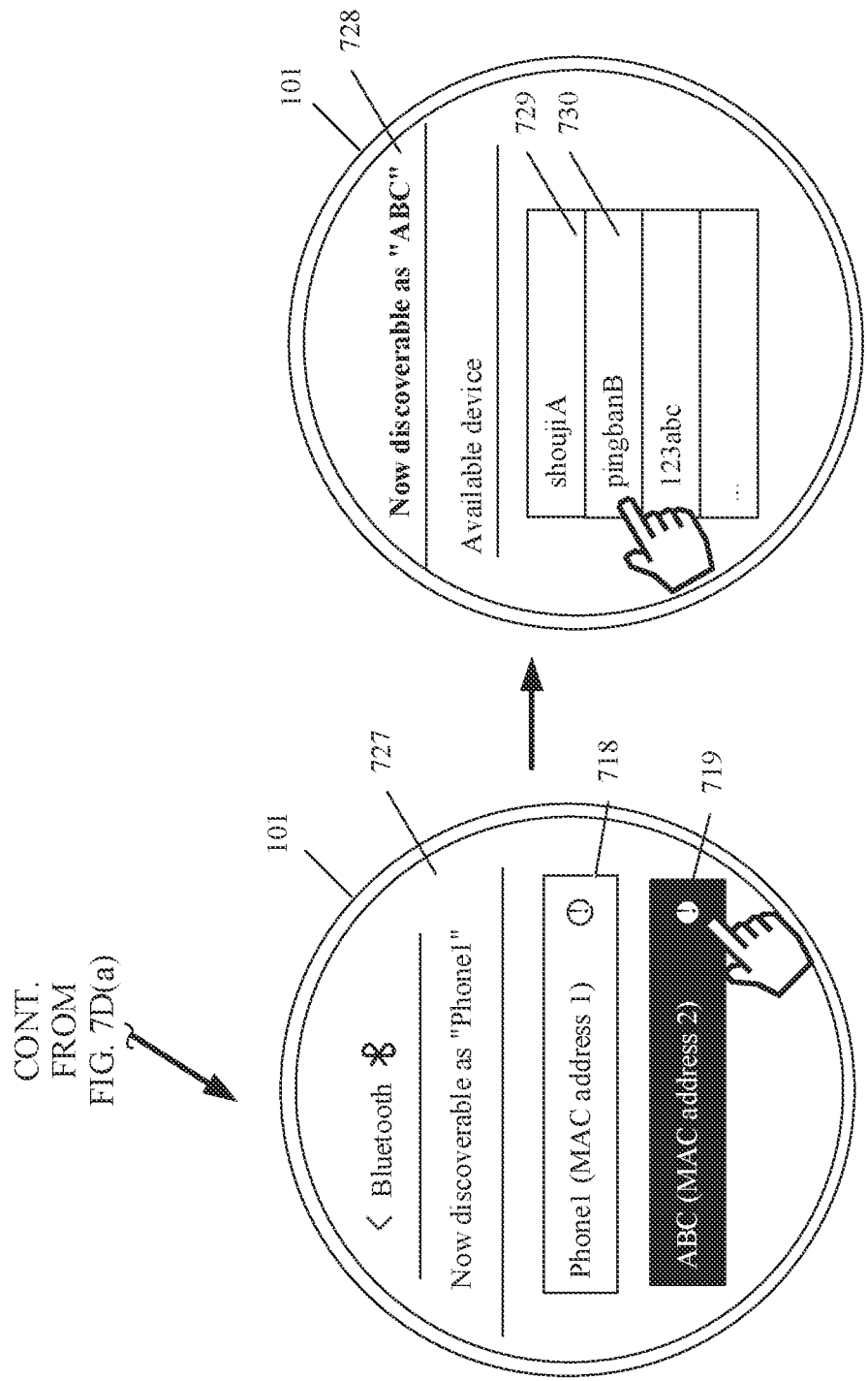

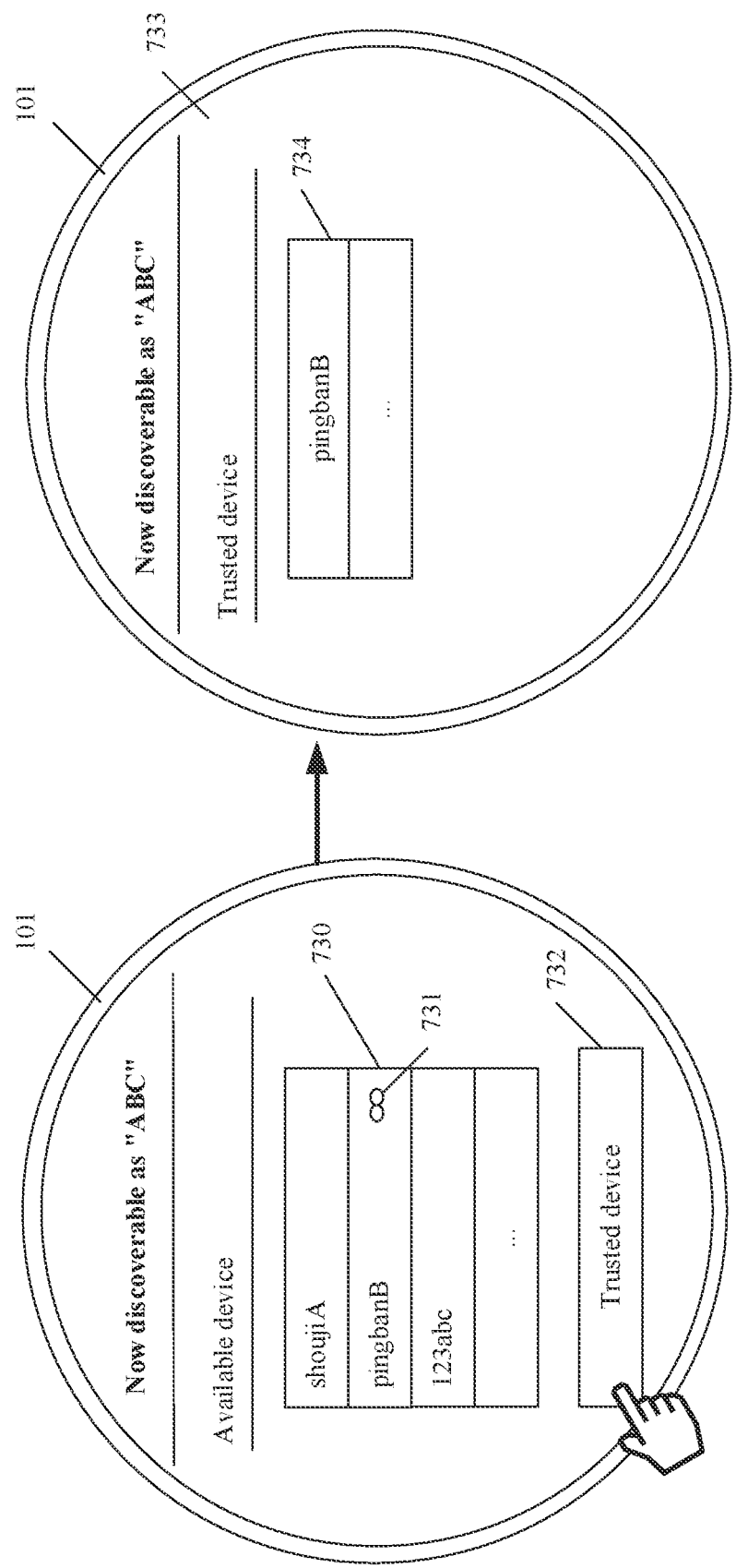

WEARABLE DEVICE AND ACTIVITY DATA COLLECTION METHOD

CROSS-REFERENCE TO RELATED APPLICATIONS

This application is a U.S. National Stage of International Patent Application No. PCT/CN2020/079150 filed on Mar. 13, 2020, which claims priority to Chinese Patent Application No. 201910224314.2 filed on Mar. 22, 2019. Both of the aforementioned applications are hereby incorporated by reference in their entireties.

TECHNICAL FIELD

This application relates to the field of communications technologies, and in particular, to a wearable device and an activity data collection method.

BACKGROUND

A wearable device is a portable device that can be worn on a body, a shoe or a suit, or another accessory of a user. Currently, the wearable device may be classified into a wristband device, a motion sensor device, and the like. The wristband device may be configured to monitor daily activity data of the user. For example, the daily activity data may include data such as a quantity of steps, a heart rate, and sleep. The motion sensing device may be configured to monitor running activity data of the user, for example, data such as a touch-ground time, a touch-ground impact, and a touch-ground manner generated when the user runs.

In different cases, the user needs to wear different wearable devices to monitor corresponding data. For example, the user wears the wristband device daily to monitor the daily activity data, and the user wears the motion sensing device during running to monitor the running activity data. In this case, the user needs to buy two wearable devices, causing relatively high costs.

SUMMARY

Embodiments of this application provide a wearable device and an activity data collection method, to collect both daily activity data and running activity data of a user. In other words, the wearable device has a capability of collecting both the daily activity data and the running activity data. Therefore, the user can have use experience of the foregoing two wearable devices when the user only needs to purchase one wearable device.

According to a first aspect, an embodiment of this application provides an activity data collection method. The method may be applied to a wearable device, and the wearable device includes at least two working modes. The at least two working modes include a first working mode and a second working mode. The method may include: The wearable device receives a user operation; the wearable device starts the first working mode in response to a first operation of a user to collect first activity data; and the wearable device starts the second working mode in response to a second operation of the user to collect second activity data. The first activity data is daily activity data of the user, and the second activity data is professional exercise data of the user.

In this embodiment of this application, the wearable device collects different types of activity data (for example, the daily activity data and the professional exercise data) in different working modes. In other words, the wearable device may be configured to collect both the first activity data and the second activity data of the user. That the wearable device may collect different activity data in different working modes means that the wearable device has a capability of collecting two types of activity data. Therefore, the user can have use experience of the foregoing two wearable devices when the user only needs to purchase one wearable device.

With reference to the first aspect, in a possible design manner, the wearable device includes a device body, a first carrier, and a second carrier. Both the first carrier and the second carrier are configured to fasten the device body. The device body is worn on a body, a shoe or a suit, or another accessory of the user by using the first carrier or the second carrier. If the device body is fastened to the first carrier, the wearable device is in the first working mode. If the device body is fastened to the second carrier, the wearable device is in the second working mode. For example, the first carrier may be a watchband, and the second carrier may be a shoe buckle.

With reference to the first aspect, in another possible design manner, the device body includes a first-type sensor and a second-type sensor. The wearable device may start the first-type sensor in response to the first operation, so that the wearable device works in the first working mode. The wearable device may start the second-type sensor in response to the second operation, so that the wearable device works in the second working mode. The first-type sensor is configured to collect the first activity data, and the second-type sensor is configured to collect the second activity data. In other words, the wearable device may start different types of sensors in different working modes to collect different activity data. The first-type sensor is different from the second-type sensor.

With reference to the first aspect, in another possible design manner, the first activity data includes at least one or more types of the following data: a quantity of steps, a heart rate, and a sleep parameter of the user.

With reference to the first aspect, in another possible design manner, if the second working mode is a running mode, the second activity data includes at least one or more types of the following data, a touch-ground time, a touch-ground impact, a leg swing angle, and a valgus amplitude generated when the user runs.

With reference to the first aspect, in another possible design manner, if the second working mode is a basketball mode, the second activity data includes at least one or more types of the following data: a running distance, a quantity of jumps, and a jump height.

With reference to the first aspect, in another possible design manner, the first-type sensor may be a sensor that integrates modules such as a step quantity monitoring module, a heart rate monitoring module, and a sleep monitoring module. For example, the first-type sensor may be referred to as a gravity sensor. The gravity sensor integrates the modules such as the step quantity monitoring module, the heart rate monitoring module, and the sleep monitoring module. Alternatively, the first-type sensor may include a plurality of sensors. For example, the first-type sensor includes a sensor configured to monitor a quantity of steps, a sensor configured to monitor a heart rate, and a sensor configured to monitor sleep. In other words, the step quantity monitoring module, the heart rate monitoring module, and the sleep monitoring module are all independent sensors.

With reference to the first aspect, in another possible design manner, the second working mode may be the running mode. In an implementation, the second-type sensor may be a sensor that integrates modules such as a touch-ground time monitoring module, a touch-ground impact monitoring module, a swing angle monitoring module, and a valgus amplitude monitoring module. For example, the second-type sensor may be referred to as a running sensor. The running sensor integrates the modules such as the touch-ground time monitoring module, the touch-ground impact monitoring module, the swing angle monitoring module, and the valgus amplitude monitoring module. In another implementation, the second-type sensor may include a plurality of sensors. For example, the second-type sensor includes a sensor configured to monitor a touch-ground time, a sensor configured to monitor a touch-ground impact, a sensor configured to monitor a swing angle, and a sensor configured to monitor a valgus amplitude. In other words, the touch-ground time monitoring module, the touch-ground impact monitoring module, the swing angle monitoring module, and the valgus amplitude monitoring module are all independent sensors.

With reference to the first aspect, in another possible design manner, the second working mode may be the basketball mode. The second-type sensor may be a sensor that integrates modules such as a running distance monitoring module, a jump quantity monitoring module, and a jump height monitoring module. In another implementation, the second-type sensor may include a plurality of sensors. For example, the second-type sensor includes a sensor configured to monitor a running distance, a sensor configured to monitor a quantity of jumps, and a sensor configured to monitor a jump height. The running distance monitoring module, the jump quantity monitoring module, and the jump height monitoring module are all independent sensors.

With reference to the first aspect, in another possible design manner (a design manner a), the first operation is that the device body is fastened to the first carrier, and the second operation is that the device body is fastened to the second carrier. In this design manner, if the user fastens the device body to the first carrier (for example, the watchband), the device body may start the first-type sensor in response to the first operation. If the user fastens the device body to the second carrier (for example, the shoe buckle), the device body may start the second-type sensor in response to the second operation.

With reference to the first aspect, in another possible design manner (a design manner b), the device body further includes a first preset hardware switch or key, and the first operation and the second operation are different operations performed by the user on the first preset hardware switch or key. Alternatively, the device body further includes a display, and the first operation and the second operation are different operations performed by the user on a first preset button or option displayed on the display. In this design manner, the device body is fastened to the first carrier, but it does not trigger the device body to start the first-type sensor. The device body is fastened to the second carrier, but it does not trigger the device body to start the second-type sensor.

With reference to the first aspect, in another possible design manner, the device body further includes a switching circuit. The switching circuit includes a detection contact and a detection port. The first carrier and the second carrier each include a metal contact. The device body may detect a contact voltage of the detection port of the switching circuit. In response to the first operation, when the detection contact of the switching circuit is in contact with the metal contact of the first carrier, the device body detects that the contact voltage is a first voltage value, and the device body starts the first-type sensor. In response to the second operation, when the detection contact of the switching circuit is in contact with the metal contact of the second carrier, the device body detects that the contact voltage is a second voltage value, and the device body starts the second-type sensor.

It should be noted that, in the design manner a, if the device body is fastened to the first carrier, when the detection contact of the switching circuit is in contact with the metal contact of the first carrier, the device body detects that the contact voltage is the first voltage value, and the device body starts the first-type sensor. If the device body is fastened to the second carrier, when the detection contact of the switching circuit is in contact with the metal contact of the second carrier, the device body detects that the contact voltage is the second voltage value, and the device body starts the second-type sensor.

In the design manner b, the device body is fastened to the first carrier, the detection contact of the switching circuit is not in contact with the metal contact of the first carrier, and the device body does not detect that the contact voltage is the first voltage value. Instead, after the device body is fastened to the first carrier, if the user performs the first operation (for example, a click operation) on the first preset hardware switch or key, or the first preset button or option, the detection contact of the switching circuit is in contact with the metal contact of the first carrier, and the device body can detect that the contact voltage is the first voltage value. In this case, the device body starts the first-type sensor. Likewise, the device body is fastened to the second carrier, the detection contact of the switching circuit is not in contact with the metal contact of the second carrier, and the device body does not detect that the contact voltage is the second voltage value. Instead, after the device body is fastened to the second carrier, if the user performs the second operation (for example, a double-click operation) on the first preset hardware switch or key, or the first preset button or option, the detection contact of the switching circuit is in contact with the metal contact of the second carrier, and the device body can detect that the contact voltage is the second voltage value. In this case, the device body starts the second-type sensor.

With reference to the first aspect, in another possible design manner, after the wearable device starts the first working mode, the wearable device may present the first activity data to the user; or the wearable device may send the first activity data to an electronic device through a wireless connection to the electronic device, so that the electronic device presents the first activity data to the user.

With reference to the first aspect, in another possible design manner, after the wearable device starts the second working mode, the wearable device may present the second activity data to the user; or the wearable device may send the second activity data to the electronic device through the wireless connection to the electronic device, so that the electronic device presents the second activity data to the user.

With reference to the first aspect, in another possible design manner, before the wearable device starts the first-type sensor or the second-type sensor, the wearable device may receive, through the wireless connection to the electronic device, a first message sent by the electronic device. The first message is used to indicate the wearable device to start to collect activity data of the user. That the wearable device starts the first-type sensor includes: The wearable device starts the first-type sensor in response to the first message. That the wearable device starts the second-type sensor includes: The wearable device starts the second-type sensor in response to the first message.

With reference to the first aspect, in another possible design manner, the device body may include at least two media access control (media access control, MAC) addresses. The at least two MAC addresses may include a first MAC address and a second MAC address.

With reference to the first aspect, in another possible design manner, the wearable device uses the first MAC address in response to a third operation of the use, and the wearable device uses the second MAC address in response to a fourth operation of the user.

The third operation may be that the device body is fastened to the first carrier, and the fourth operation may be that the device body is fastened to the second carrier. In other words, the wearable device may use the first MAC address in the first working mode (that is, when the first-type sensor is started), and use the second MAC address in the first working mode (that is, when the second-type sensor is started).

With reference to the first aspect, in another possible design manner, the device body further includes a second preset hardware switch or key, and the third operation and the fourth operation are different operations performed by the user on the second preset hardware switch or key. The wearable device displays a Bluetooth setting interface in response to a fifth operation of the user. The Bluetooth setting interface includes an option corresponding to the first MAC address and an option corresponding to the second MAC address. The third operation is a selection operation performed by the user on the option corresponding to the first MAC address. The fourth operation is a selection operation performed by the user on the option corresponding to the second MAC address.

According to a second aspect, an embodiment of this application provides a wearable device. A wearable device includes a processor and a memory. The memory and the processor are coupled. The processor includes at least two working modes. The at least two working modes include a first working mode and a second working mode. The memory is configured to store computer program code. The computer program code includes computer instructions. When the processor executes the computer instructions, the wearable device performs the following operations: the processor is configured to: receive a user operation; start the first working mode in response to a first operation of a user to collect first activity data, where the first activity data is daily activity data of the user; and start the second working mode in response to a second operation of the user to collect second activity data, where the second activity data is professional exercise data of the user.

With reference to the second aspect, in a possible design manner, the wearable device includes the device body, a first carrier, and a second carrier. The processor is included in the device body. Both the first carrier and the second carrier are configured to fasten the device body. The device body is worn on a body, a shoe or a suit, or another accessory of the user by using the first carrier or the second carrier. If the device body is fastened to the first carrier, the wearable device is in the first working mode. If the device body is fastened to the second carrier, the wearable device is in the second working mode.

With reference to the second aspect, in another possible design manner, the device body includes a first-type sensor and a second-type sensor. That the processor is configured to start the first working mode in response to a first operation of a user to collect the first activity data includes, the processor is configured to start the first-type sensor in response to the first operation, so that the wearable device works in the first working mode. The first-type sensor is configured to collect the first activity data.

That the processor is configured to start the second working mode in response to a second operation of the user to collect the second activity data includes: the processor is configured to start the second-type sensor in response to the second operation, so that the wearable device works in the second working mode. The second-type sensor is configured to collect the second activity data. The first-type sensor is different from the second-type sensor.

With reference to the second aspect, in another possible design manner, the first activity data includes at least one or more types of the following data: a quantity of steps, a heart rate, and a sleep parameter of the user. If the second working mode is a running mode, the second activity data includes at least one or more types of the following data: a touch-ground time, a touch-ground impact, a leg swing angle, and a valgus amplitude generated when the user runs; or if the second working mode is a basketball mode, the second activity data includes at least one or more types of the following data a running distance, a quantity of jumps, and a jump height.

With reference to the second aspect, in another possible design manner, the first operation is that the device body is fastened to the first carrier, and the second operation is that the device body is fastened to the second carrier.

With reference to the second aspect, in another possible design manner, the device body further includes a switching circuit. The switching circuit includes a detection contact and a detection port. The first carrier and the second carrier each include a metal contact. The processor is further configured to detect a contact voltage of the detection port of the switching circuit. That the processor is configured to start the first working mode in response to a first operation of a user to collect the first activity data includes: the processor is configured to: in response to the first operation, when the detection contact of the switching circuit is in contact with the metal contact of the first carrier, detect that the contact voltage is a first voltage value, and start the first working mode to collect the first activity data.

That the processor is configured to start the second working mode in response to a second operation of the user to collect the second activity data includes: the processor is configured to: in response to the second operation, when the detection contact of the switching circuit is in contact with the metal contact of the second carrier, detect that the contact voltage is a second voltage value, and start the second working mode to collect the second activity data.

With reference to the second aspect, in another possible design manner, the device body further includes a first preset hardware switch or key, and the first operation and the second operation are different operations performed by the user on the first preset hardware switch or key. Alternatively, the device body further includes a display, and the first operation and the second operation are different operations performed by the user on a first preset button or option displayed on the display.

With reference to the second aspect, in another possible design manner, the device body further includes a switching circuit. The switching circuit includes a detection contact and a detection port. The processor is further configured to detect a contact voltage of the detection port of the switching circuit. That the processor is configured to start the first working mode in response to a first operation of a user to collect the first activity data includes: the processor is configured to: in response to the first operation, detect that the contact voltage is a first voltage value, and start the first working mode to collect the first activity data. That the processor is configured to start the second working mode in response to a second operation of the user to collect the second activity data includes: the processor is configured to: in response to the second operation, detect that the contact voltage is a second voltage value, and start the second working mode to collect the second activity data.

With reference to the second aspect, in another possible design manner, the processor is further configured to present the first activity data to the user after starting the first working mode; or the device body further includes a wireless communications module, where the wireless communications module is configured to establish wireless connection to an electronic device and send the first activity data to the electronic device through the wireless connection, so that the electronic device presents the first activity data to the user.

With reference to the second aspect, in another possible design manner, the processor is further configured to present the second activity data to the user after starting the second working mode; or the device body further includes the wireless communications module, where the wireless communications module is configured to establish the wireless connection to the electronic device and send the second activity data to the electronic device through the wireless connection, so that the electronic device presents the second activity data to the user.

With reference to the second aspect, in another possible design manner, the wireless communications module in the device body is further configured to; before the processor starts the first working mode or the second working mode, receive, through the wireless connection to the electronic device, a first message sent by the electronic device, where the first message is used to indicate the wearable device to start to collect activity data of the user. That the processor is configured to start the first working mode in response to a first operation of a user to collect the first activity data includes: the processor is specifically configured to: after the wireless communications module receives the first message, start the first working mode in response to the first operation to collect the first activity data. That the processor is configured to start the second working mode in response to a second operation of the user to collect the second activity data includes: the processor is specifically configured to: after the wireless communications module receives the first message, start the second working mode in response to the second operation to collect the second activity data.

With reference to the second aspect, in another possible design manner, the processor is provided with at least two MAC addresses, and the at least two MAC addresses include a first MAC address and a second MAC address.

With reference to the second aspect, in another possible design manner, the processor is further configured to: control the wireless communications module to use the first MAC address in response to a third operation of the user; and control the wireless communications module to use the second MAC address in response to a fourth operation of the user.

With reference to the second aspect, in another possible design manner, the third operation is that the device body is fastened to the first carrier, and the fourth operation is that the device body is fastened to the second carrier.

With reference to the second aspect, in another possible design manner, the device body further includes a preset switch, and the third operation and the fourth operation are different operations performed by the user on the preset switch; or the device body further includes the display. The processor is configured to display a Bluetooth setting interface on the display in response to a fifth operation of the user. The Bluetooth setting interface includes an option corresponding to the first MAC address and an option corresponding to the second MAC address. The third operation is a selection operation performed by the user on the option corresponding to the first MAC address. The fourth operation is a selection operation performed by the user on the option corresponding to the second MAC address.

According to a third aspect, an embodiment of this application provides a computer storage medium. The computer storage medium includes computer instructions, and when the computer instructions are run on an electronic device, a processor of the electronic device is enabled to perform the method according to any one of the first aspect or the possible design manners of the first aspect.

According to a fourth aspect, an embodiment of this application provides a computer program product. When the computer program product runs on a computer, the computer is enabled to perform the method according to any one of the first aspect and the possible design manners of the first aspect.

It may be understood that, for beneficial effects that can be achieved by the wearable device in the second aspect and any possible design manner of the second aspect, the computer storage medium in the third aspect, and the computer program product in the fourth aspect, refer to beneficial effects in the first aspect and any possible design manner of the first aspect. Details are not described herein again.

According to a fifth aspect, an embodiment of this application provides an electronic device. The electronic device includes a processor, a memory, and a Bluetooth module. The processor, the memory, and the Bluetooth module are coupled. The processor is provided with at least two MAC addresses, and the at least two MAC addresses include a first MAC address and a second MAC address. The memory is configured to store computer program code. The computer program code includes computer instructions. When the processor executes the computer instructions, the electronic device performs the following operations: the processor is configured to: control the Bluetooth module to use the first MAC address in response to a third operation of a user; and control the Bluetooth module to use the second MAC address in response to a fourth operation of the user.

With reference to the fifth aspect, in a possible design manner, the electronic device further includes a preset switch, and the third operation and the fourth operation are different operations performed by the user on the preset switch.

With reference to the fifth aspect, in another possible design manner, the electronic device further includes a display. The processor is further configured to control the display to display a Bluetooth setting interface in response to a fifth operation of the user. The Bluetooth setting interface includes an option corresponding to the first MAC address and an option corresponding to the second MAC address. The third operation is a selection operation performed by the user on the option corresponding to the first MAC address in the Bluetooth setting interface, and the fourth operation is a selection operation performed by the user on the option corresponding to the second MAC address in the Bluetooth setting interface.

According to a sixth aspect, an embodiment of this application provides a computer storage medium. The computer storage medium includes computer instructions, and when the computer instructions are run on the electronic device according to the fifth aspect and the possible design manners of the fifth aspect, the electronic device is enabled to perform a function of a corresponding module.

According to a seventh aspect, an embodiment of this application provides a computer program product. When the computer program product runs on a computer, the computer is enabled to perform a function of a corresponding module in the electronic device according to the fifth aspect and the possible design manners of the fifth aspect.

It may be understood that, for beneficial effects that can be achieved by the electronic device according to the fifth aspect, the computer storage medium according to the sixth aspect, and the computer program product according to the seventh aspect, refer to beneficial effects in the first aspect and any possible design manner of the first aspect. Details are not described herein again.

BRIEF DESCRIPTION OF DRAWINGS

FIG. 5A and FIG. 5B are a flowchart of an activity data collection method according to an embodiment of this application;

FIG. 7C(a) and FIG. 7C(b) are a schematic diagram of an example of another Bluetooth interface according to an embodiment of this application:

FIG. 7D(a) to FIG. 7D(c) are a schematic diagram of an example of another Bluetooth interface according to an embodiment of this application:

FIG. 7E(a) and FIG. 7E(b) are a schematic diagram of an example of another Bluetooth interface according to an embodiment of this application:

DESCRIPTION OF EMBODIMENTS

Figure 1:
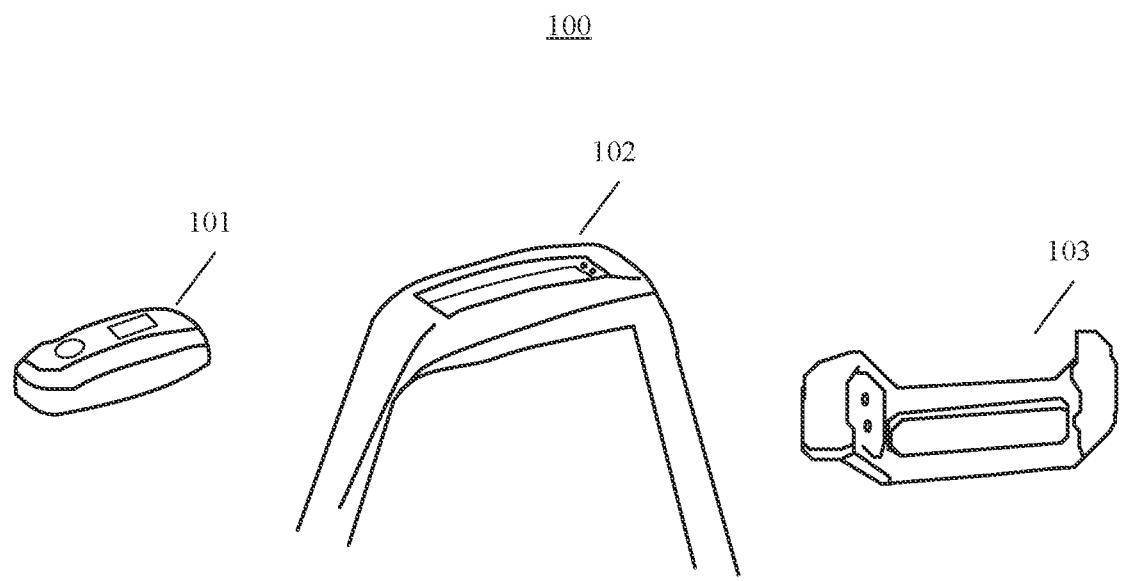
FIG. 1 is a schematic diagram of a product model of a wearable device according to an embodiment of this application.

The embodiments of this application provide a wearable device. The wearable device may include at least two types of monitoring modules (for example, sensors). For example, the wearable device may include a first-type monitoring module (namely, a first-type sensor) and a second-type monitoring module (namely, a second-type sensor). The first-type monitoring module is configured to collect first activity data (for example, daily activity data of a user). The second-type monitoring module is configured to collect second activity data (for example, running activity data or basketball activity data of the user).

The wearable device may start different types of monitoring modules in different working modes. For example, the wearable device starts the first-type monitoring module in a first working mode (for example, a wristband mode) to collect the first activity data, and starts the second-type monitoring module in a second working mode (for example, a running mode or a basketball mode) to collect the second activity data.

For example, the first-type monitoring module (namely, the first-type sensor) may include a step quantity monitoring module, a heart rate monitoring module, and a sleep monitoring module. The daily activity data may include data such as a quantity of steps, a heart rate, and sleep of the user.

In an implementation, the first-type sensor may be a sensor that integrates modules such as the step quantity monitoring module, the heart rate monitoring module, and the sleep monitoring module. For example, the first-type sensor may be referred to as a gravity sensor. The gravity sensor integrates modules such as the step quantity monitoring module, the heart rate monitoring module, and the sleep monitoring module.

In another implementation, the first-type sensor may include a plurality of sensors. For example, the first-type sensor includes a sensor configured to monitor a quantity of steps, a sensor configured to monitor a heart rate, and a sensor configured to monitor sleep. In other words, the step quantity monitoring module, the heart rate monitoring module, and the sleep monitoring module are all independent sensors.

In some embodiments, the second working mode may be the running mode. The second-type monitoring module (namely, the second-type sensor) may include a touch-ground time monitoring module, a touch-ground impact monitoring module, a swing angle monitoring module, a valgus amplitude monitoring module, and the like. The running activity data may include data such as a touch-ground time, a touch-ground impact, a leg swing angle, and a valgus amplitude generated when the user runs.

In an implementation, the second-type sensor may be a sensor that integrates modules such as the touch-ground time monitoring module, the touch-ground impact monitoring module, the swing angle monitoring module, and the valgus amplitude monitoring module. For example, the second-type sensor may be referred to as a running sensor. The running sensor integrates modules such as the touch-ground time monitoring module, the touch-ground impact monitoring module, the swing angle monitoring module, and the valgus amplitude monitoring module.

In another implementation, the second-type sensor may include a plurality of sensors. For example, the second-type sensor includes a sensor configured to monitor a touch-ground time, a sensor configured to monitor a touch-ground impact, a sensor configured to monitor a swing angle, and a sensor configured to monitor a valgus amplitude. In other words, the touch-ground time monitoring module, the touch-ground impact monitoring module, the swing angle monitoring module, and the valgus amplitude monitoring module are all independent sensors.

In some embodiments, the second working mode may be the basketball mode. The second-type monitoring module (namely, the second-type sensor) may include a running distance monitoring module, a jump quantity monitoring module, a jump height monitoring module, and the like. The running activity data may include data such as a running distance, a quantity of jumps, and a jump height generated when the user plays basketball.

In an implementation, the second-type sensor may be a sensor that integrates modules such as the running distance monitoring module, the jump quantity monitoring module, and the jump height monitoring module. In another implementation, the second-type sensor may include a plurality of sensors. For example, the second-type sensor includes a sensor configured to monitor a running distance, a sensor configured to monitor a quantity of jumps, and a sensor configured to monitor jump height. The running distance monitoring module, the jump quantity monitoring module, and the jump height monitoring module are all independent sensors.

In conclusion, the wearable device not only may be configured to collect the daily activity data of the user, but also may be configured to collect the running activity data, the basketball activity data, and the like of the user. That the wearable device may collect different activity data in different working modes means that the wearable device has a capability of collecting both the daily activity data and the running activity data. Therefore, the user can have use experience of the foregoing two wearable devices when the user only needs to purchase one wearable device.

It should be noted that, in the embodiments of this application, the wearable device and an activity data collection method provided in the embodiments of this application are described by using an example in which the first working mode is the wristband mode and the second working mode is the running mode.

FIG. 1 is a schematic diagram of a product model of a wearable device according to an embodiment of this application. As shown in FIG. 1, the wearable device 100 may include a device body 101, a first carrier (for example, a watchband) 102, and a second carrier (for example, a shoe buckle) 103. The device body 101 includes the first-type monitoring module (namely, the first-type sensor) and the second-type monitoring module (namely, the second-type sensor).

Both the first carrier 102 and the second carrier 103 are configured to fasten the device body 101. The device body 101 is worn on a body, a shoe or a suit, or another accessory of a user by using the first carrier 102 or the second carrier 103.

Figures 2A, 2B:
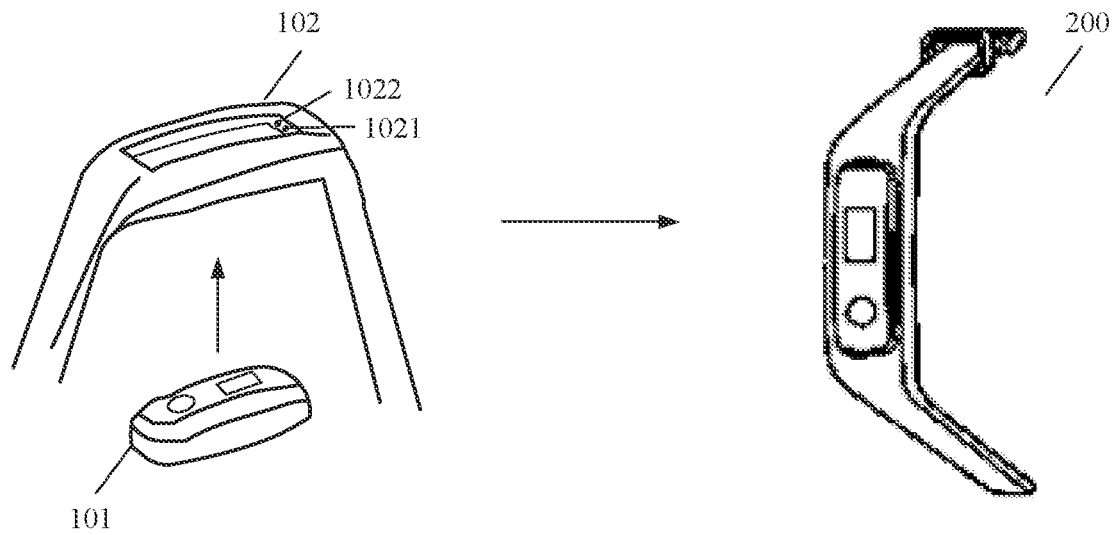
FIG. 2(a) and FIG. 2(b) are a schematic diagram of examples of a device body and a first carrier according to an embodiment of this application.

For example, the first carrier 102 is the watchband. As shown in FIG. 2(a), the user fastens the device body 101 to the watchband 102, to obtain a wristband 200 shown in FIG. 2(b). The user can wear the wrist band 200 on a wrist or an ankle. The wristband 200 (namely, the device body 101) may be configured to collect daily activity data of the user.

Figure 3A:
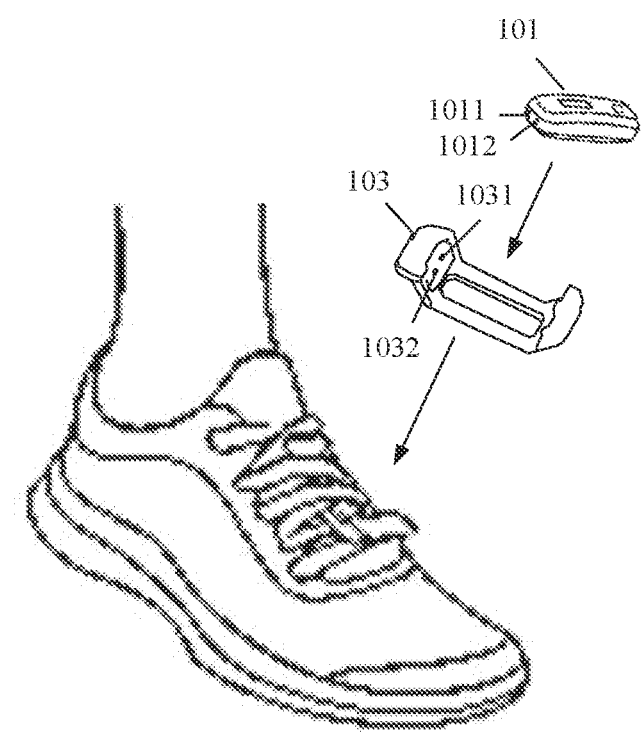
FIG. 3(a) and FIG. 3(b) are a schematic diagram of examples of a device body and a second carrier according to an embodiment of this application.
Figure 3B:
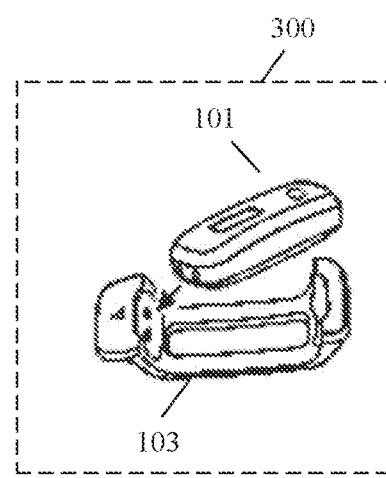

For another example, the second carrier 103 is the shoe buckle. As shown in FIG. 3(b), the user fastens the device body 101 to the shoe buckle 103, to obtain a motion sensing device 300 shown in the figure. For example, as shown in FIG. 3(a), the user may fasten the shoe buckle 103 to a shoelace (for example, attach the shoe buckle 103 underneath the shoelace). Then, the device body 101 is fastened to the shoe buckle 103. In this way, the motion sensing device 300 may be fastened to the shoe of the user.

In some embodiments, the first carrier 102 and the second carrier 103 may not only be used to fasten the device body 101. The first carrier 102 and the second carrier 103 may further include one or more metal contacts.

For example, as shown in FIG. 2(a), the first carrier 102 includes a metal contact 1021 and a metal contact 1022. After the device body 101 is fastened to the first carrier 102, the metal contact 1021 and the metal contact 1022 of the first carrier 102 are in contact with detection contacts of the device body 101. The detection contact is also a metal contact.

As shown in FIG. 3(a), the second carrier 103 includes a metal contact 1031 and a metal contact 1032. After the device body 101 is fastened to the second carrier 103, the metal contact 1031 and the metal contact 1032 of the second carrier 103 are in contact with the detection contacts (namely, metal contacts) of the device body 101.

For example, as shown in FIG. 3(a), the device body 101 may include a detection contact 1011 and a detection contact 1012. After the device body 101 is fastened to the second carrier 103, the metal contact 1031 may be in contact with the detection contact 1011, and the metal contact 1032 may be in contact with the detection contact 1012.

When the detection contact of the device body 101 is in contact with the metal contact of the first carrier 102, a detection port of the device body 101 may detect a first voltage value. That is, a contact voltage of the detection port is the first voltage value. When the detection contact of the device body 101 is in contact with the metal contact of the second carrier 103, the detection port of the device body 101 may detect a second voltage value. That is, the contact voltage of the detection port is the second voltage value.

The first voltage value is different from the second voltage value. The device body 101 may determine, based on a voltage value of the detected contact voltage, a carrier to which the device body 101 is currently fastened. For example, if the contact voltage is the first voltage value, the device body 101 may determine that the device body 101 is fastened to the first carrier 102. If the contact voltage is the second voltage value, the device body 101 may determine that the device body 101 is fastened to the second carrier 103.

It should be noted that the first carrier 102 and the second carrier 103 may be fastened to the device body 101 in a clamping manner or another physical connection manner. A specific manner for fastening the device body 101 to the first carrier 102 and the second carrier 103 is not limited in this embodiment of this application.

Figure 4A:
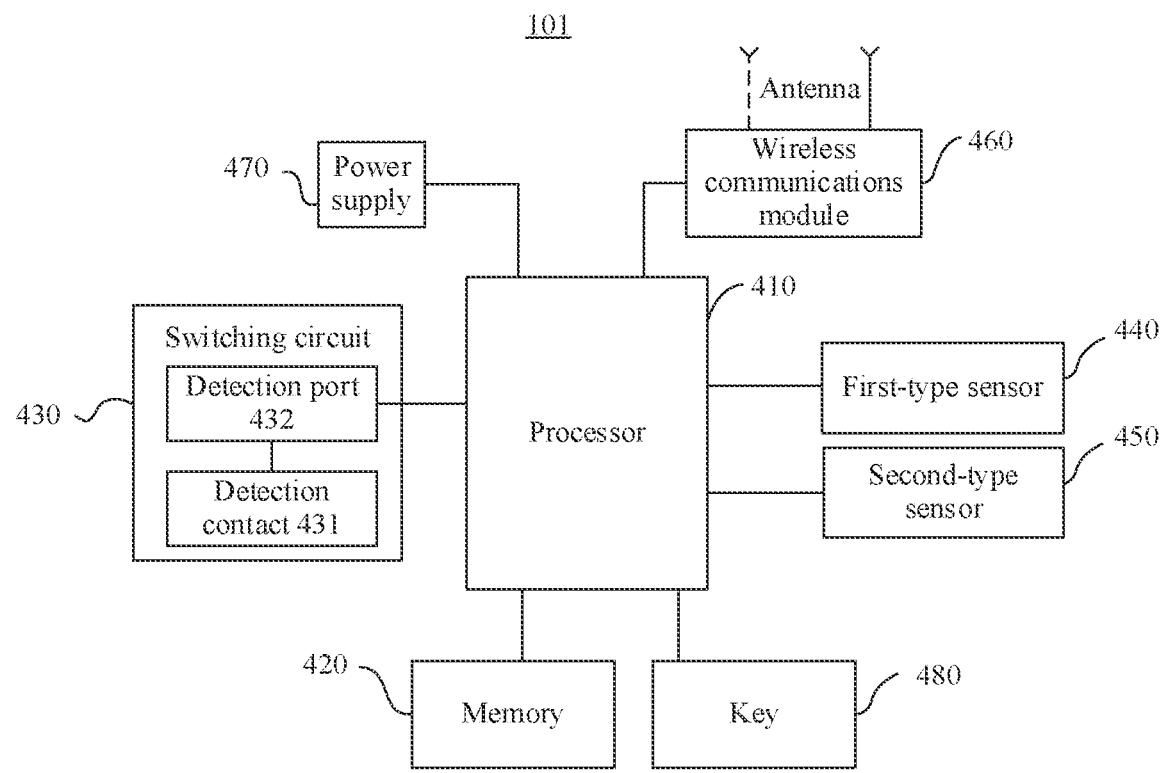
FIG. 4A is a schematic structural composition diagram of a device body according to an embodiment of this application.

FIG. 4A is a schematic diagram of a structure of a device body according to an embodiment of this application. As shown in FIG. 4A, the device body 101 shown in any one of FIG. 1 to FIG. 3 may include a processor 410, a memory 420, a switching circuit 430, a first-type sensor 440, a second-type sensor 450, a wireless communications module 460, an antenna, and a power supply 470.

The memory 420 may be configured to store application program code, for example, application program code used to start a first-type sensor (namely, a first-type monitoring module) 440 or a second-type sensor (namely, a second-type monitoring module) 450 in response to a user operation (for example, a first operation or a second operation), application program code used to detect a contact voltage of the switching circuit 430, and start a corresponding sensor based on the contact voltage, and application program code used to establish a wireless connection to an electronic device. The processor 410 may control execution of the foregoing application program code, to implement functions of a wearable device in this embodiment of this application.

The memory 420 may further store a Bluetooth address used to uniquely identify the wearable device. In addition, the memory 420 may further store connection data of an electronic device that is successfully paired with the wearable device (namely, the device body 101) before. For example, the connection data may be a Bluetooth address of the electronic device that is successfully paired with the wearable device. The wearable device can be automatically paired with the electronic device based on the connection data, and there is no need to configure a connection between the wearable device and the electronic device. For example, validity verification is not required. The Bluetooth address may be a MAC address.

In some embodiments, the wearable device (namely, the device body 101) provided in this embodiment of this application may include two MAC addresses, for example, a MAC address 1 and a MAC address 2. The wearable device may establish a wireless connection (for example, a Bluetooth connection) to a plurality of electronic devices by using the two MAC addresses. For example, the wearable device may establish a wireless connection to an electronic device A by using the MAC address 1, and establish a wireless connection to an electronic device B by using the MAC address 2.

The switching circuit 430 includes a detection contact 431 and a detection port 432. For example, the detection contact 431 may include the detection contact 1011 and the detection contact 1012 shown in FIG. 3(*a*).

The detection contact 431 may be disposed on a housing of the device body 101. When the device body 101 is fastened to a first carrier 102, the detection contact 431 may be in contact with a metal contact of the first carrier 102. When the device body 101 is fastened to a second carrier 103, the detection contact 431 may be in contact with a metal contact of the second carrier 103.

The detection port 432 is connected to the processor 410. If the detection contact 431 is in contact with the metal contact of the first carrier 102, the processor 410 may detect a first voltage value of the detection port 432 (that is, a contact voltage of the detection port 432 is the first voltage value), to determine that the device body 101 is currently fastened to the first carrier. If the detection contact 431 is in contact with the metal contact of the second carrier 103, the processor 410 may detect a second voltage value of the detection port 432 (that is, a contact voltage of the detection port 432 is the second voltage value), to determine that the device body 101 is currently fastened to the second carrier.

Figure 4B:
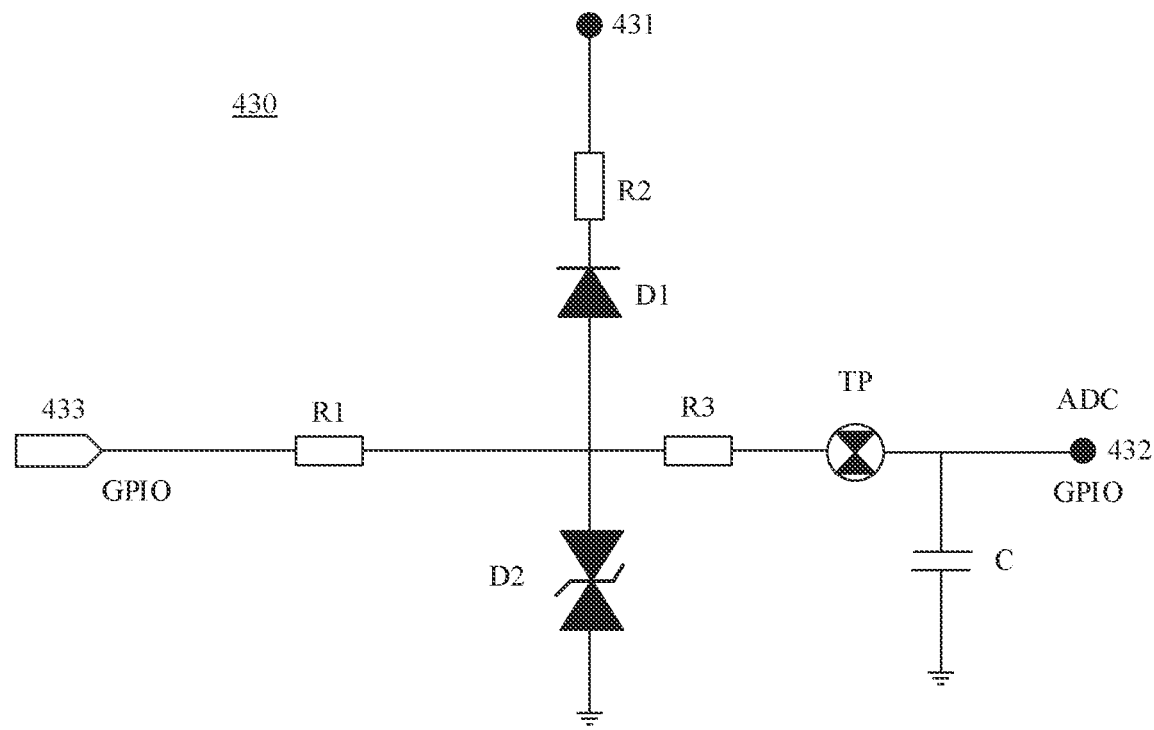
FIG. 4B is a schematic diagram of an example of a switching circuit in a device body according to an embodiment of this application.
Figure 5A:
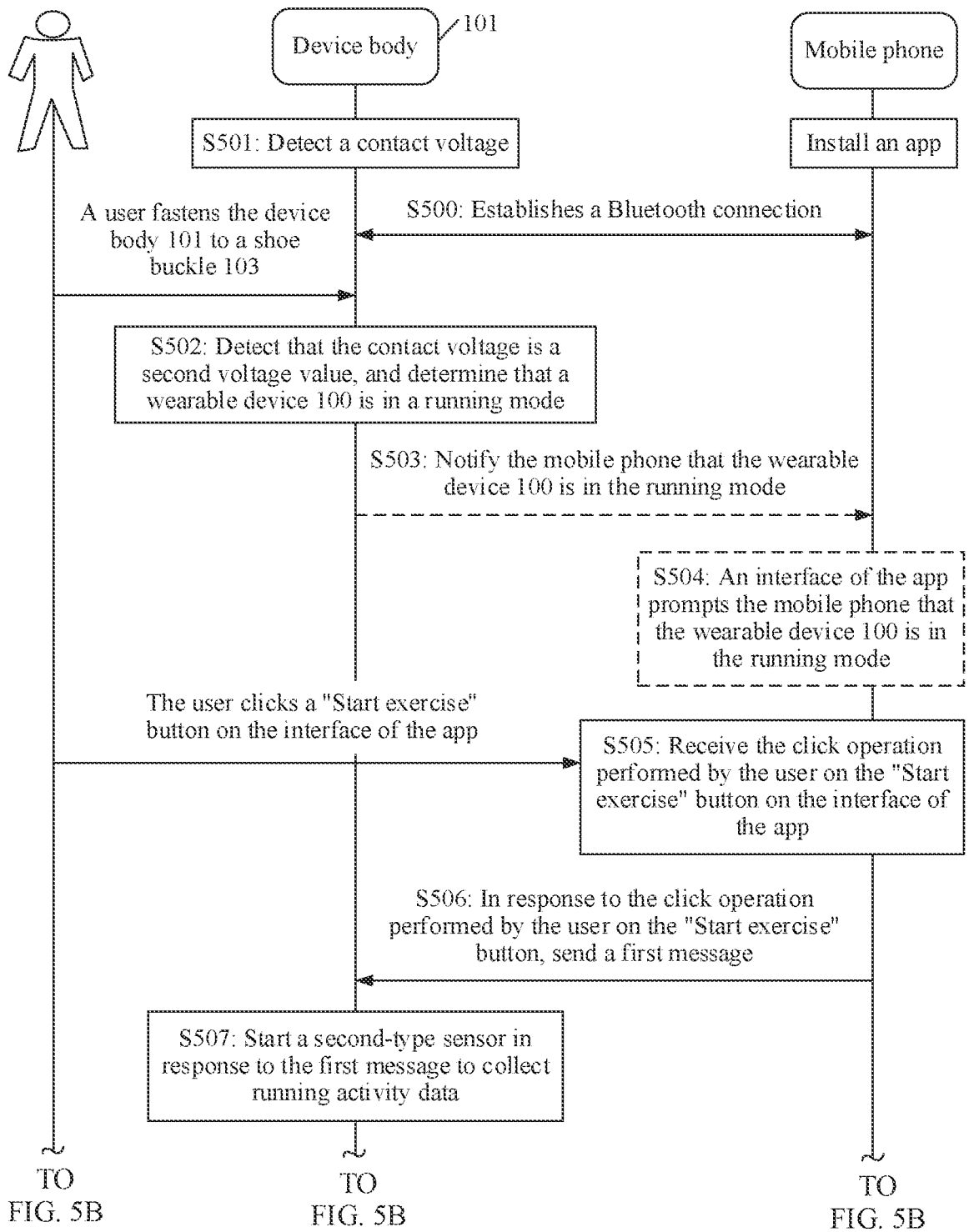

For example, FIG. 4B is a schematic diagram of an example of the switching circuit 430 according to an embodiment of this application. As shown in FIG. 4B, the switching circuit 430 may include the detection contact 431, the detection port 432, and a high-level port 433.

The high-level port 433 may be connected to the processor 410, so that the processor 410 supplies power to the switching circuit 430. Alternatively, the high-level port 433 may be connected to the power supply 470, so that the power supply 470 directly supplies power to the switching circuit 430. The detection port 432 and the high-level port 433 may be general-purpose input/output (general-purpose input/output, GPIO) interfaces.

It should be noted that, if the device body 101 is in a power-on state, the high-level port 433 is always in a high-level state. In other words, as long as the device body 101 is in the power-on state, regardless of whether the device body 101 is fastened to which carrier (the first carrier 102 or the second carrier 103), the high-level port 433 is always in the high-level state.

For example, the switching circuit 430 provided in this embodiment of this application may be an ADC voltage switching circuit. As shown in FIG. 4B, the switching circuit 430 may further include a resistor R2, a diode D1, a resistor R1, a bidirectional breakdown diode D3, a resistor R3, a capacitor C. and a hardware test point (Test Point, TP).

The detection contact 431 is connected to one end of the resistor R2, and the other end of the resistor R2 is connected to the diode D1. The other end of the diode D1 is connected to one end of the resistor R3. The other end of the resistor R3 is connected to one end of the TP. The other end of the TP is connected to the detection port 432 and one end of the capacitor C. The other end of capacitor C is grounded. The detection port 432 is connected to the processor, such as a micro control unit (Microcontroller Unit, MCU), of the device body 101. After the MCU is connected to the detection port 432, a voltage value of the hardware test point (TP) can be detected.

The other end of the diode D1, one end of the resistor R3, and one end of the resistor R1 are all connected to one end of the bidirectional breakdown (Transient Voltage Suppressor, TVS) diode D2. The other end of the resistor R1 is connected to the high-level port 433. The other end of the bidirectional breakdown diode D2 is grounded.

For example, a resistance value of the resistor R2 may be 10 kilohms, a resistance value of the resistor R1 may be 20 kilohms, and a resistance value of the resistor R3 may be 20 kilohms (Ω). A capacitance value of the capacitor C may be 1 nF (nF). The diode D1 and the TVS diode D2 are configured to protect components in the switching circuit 430. For example, the diode D1 may control a reverse current flowing from the diode D1 to R2 to be less than 1 uA, so as to protect R2 from being broken down due to an excessively large reverse current.

In some embodiments, the detection contact 431 may alternatively be a charging interface. The wearable device 100 provided in this embodiment of this application may further include a charger. The charger may charge the device body 101 by using the detection contact 431. For example, when the device body 101 is fastened to the charger, a charging interface of the charger may be in contact with the detection contact 431 to charge the device body 101. A current from the charger may enter the high-level port 433 by using the detection contact 431, to charge the device body 101.

In some other embodiments, the device body may further include a charging interface specially used for charging. The charger may charge the voltage 470 of the device body 101 by using the charging interface. When the charger charges the device body 101 by using the charging interface, one metal contact of the charger may be in contact with the detection contact 431.

In conclusion, when the detection contact 431 is in contact with the charger (for example, the charging interface or the metal contact of the charger), the processor 410 may detect a third voltage value of the detection port 432. The third voltage value is different from the first voltage value and the second voltage value.

It may be understood that the detection contact 431 may include at least three states, for example, a charging state, a wristband state, and a running state. When the detection contact 431 is in different states, contact voltages of the detection port 432 are different.

For example, when the detection contact 431 is in contact with the charging interface of the charger, the detection contact 431 is in the charging state. In this case, the contact voltage of the detection port 432 is the third voltage value.

That is, the processor 410 may detect the third voltage value at the detection port 432. For example, the third voltage value may be 1.5 V. In this case, the processor 410 does not start any type of sensor (including the first-type sensor, and the second-type sensor).

When the detection contact 431 is in contact with the metal contact of the first carrier 102, the detection contact 431 is in the wristband state. In this case, the contact voltage of the detection port 432 is the first voltage value. That is, the processor 410 may detect the first voltage value at the detection port 432, and the processor 410 may start the first-type sensor, so that the wearable device 100 works in a wristband mode. For example, the first voltage value may be 1.3 V.

When the detection contact 431 is in contact with the metal contact of the second carrier 103, the detection contact 431 is in the running state. In this case, the contact voltage of the detection port 432 is the second voltage value. That is, the processor 410 may detect the second voltage value at the detection port 432, and the processor 410 may start the second-type sensor, so that the wearable device 100 works in a running mode. For example, the second voltage value may be 0.9 V.

The wireless communications module 460 is configured to support short-distance data exchange between the wearable device 100 and various electronic devices. In some embodiments, the wireless communications module 460 may be a Bluetooth transceiver. The device body 101 of the wearable device 100 may establish the wireless connection to the electronic device by using the Bluetooth transceiver, to implement the short-distance data exchange between the wearable device 100 and the electronic device. The antenna (for example, an antenna 1) and the wireless communications module 460 are coupled, so that the wearable device 100 can communicate with another device by using a wireless communications technology.

In some embodiments, as shown in FIG. 4A, the device body 101 may further include a key 480. The key 480 may include a power key. Optionally, the key 480 may further include one or more mode keys. The one or more mode keys are used to control the device body 101 to work in the different working modes (for example, the wristband mode or the running mode).

The key 480 may be a mechanical key or a touch-sensitive key. The device body 101 may receive key input, generate key signal input related to user setting and function control of the device body 101. For example, the device body 101 may start the first-type sensor in response to a first operation of the user on the key 480. In this case, the device body 101 works in the wristband mode. The device body 101 may start the second-type sensor in response to a second operation of the user on the key 480. In this case, the device body 101 works in the running mode.

Optionally, the wireless communications module 460 may further include a wireless fidelity (wireless fidelity, Wi-Fi) module. The device body 101 of the wearable device 100 may establish the wireless connection to the electronic device by using the Wi-Fi module, to implement the short-distance data exchange between the wearable device 100 and the electronic device.

The power supply 470 may be configured to supply power to the components included in the wearable device 100. In some embodiments, the power supply 470 may be a battery, for example, a rechargeable battery.

Optionally, the device body 101 may further include a display. The display may be configured to display the activity data (for example, the daily activity data or the running activity data) collected by the sensor of the device body 101. The display may be further configured to display parameters such as time and a date.

Optionally, the device body 101 may further include a mobile communications module. The mobile communications module can provide a solution that is applied to the device body 101 and that is for wireless communication including 2G, 3G, 4G, 5G, and the like.

Optionally, the device body 101 may further include a receiver and a microphone. The receiver also referred to as an "earpiece", may be configured to convert an audio electrical signal into a sound signal and play the sound signal. The microphone 260 may also be referred to as a "mike" or a "microphone", and is configured to convert a sound signal into an audio electrical signal. The wearable device 100 may establish a wireless connection to another electronic device, and is used as an audio input/output device of the another electronic device. For example, when the wearable device 100 is used as the audio output device of the electronic device, the receiver may convert a received audio electrical signal into a sound signal and play the sound signal. When the wearable device 100 is used as the audio input device of the electronic device, in a process in which the user speaks (for example, makes a call or sends a voice message), the microphone may collect a sound signal of the user, and convert the sound signal into an audio electrical signal.

Optionally, the device body 101 may further include a SIM card interface. The SIM card interface is configured to connect to a SIM card. The SIM card may be inserted into the SIM card interface or detached from the SIM card interface, to implement contact with or separation from the wearable device 100 (namely, the device body 101). The wearable device 100 interacts with a network through the SIM card, to implement functions such as calling and data communication.

It may be understood that the structure shown in this embodiment of this application does not constitute a specific limitation on the device body 101 of the wearable device 100. The device body 101 may have more or fewer components than those shown in FIG. 4A, may have a combination of two or more components, or may have different component configurations. For example, the device body 101 may further include a component such as an indicator (which may indicate a state such as an electrical quantity of the device body 101). The components shown in FIG. 4A may be implemented in hardware, software, or a combination of hardware and software that includes one or more signal processing or application-specific integrated circuits.

An embodiment of this application provides an activity data collection method. The activity data collection method may be implemented in the wearable device 100. The wearable device 100 may include a device body 101, a first carrier 102, and a second carrier 103. The device body 101 includes a first-type sensor and a second-type sensor. The first-type sensor is configured to collect first activity data, and the second-type sensor is configured to collect second activity data.

In this embodiment of this application, if the device body 101 is fastened to the first carrier 102, the device body 101 is used to collect the first activity data of a user. In this case, the device body 101 is in a first working mode, and the first-type sensor of the device body 101 is started. If the device body 101 is fastened to the second carrier 103, the device body 101 is used to collect the second activity data of the user. In this case, the device body 101 is in a second working mode, and the second-type sensor of the device body 101 is started.

For example, in this embodiment of this application, the method provided in this embodiment of this application is described by using an example in which the first carrier 102 is the watchband 102 shown in FIG. 2(*a*), and the second carrier 103 is the shoe buckle 103 shown in FIG. 3(*a*).

The device body 101 is fastened to the watchband 102 shown in FIG. 2(*a*), to obtain the wristband 200 shown in FIG. 2(*b*). The device body 101 is fastened to the shoe buckle 103 shown in FIG. 3(*a*), to obtain the motion sensing device 300 shown in FIG. 3(*b*). Correspondingly, if the first working mode is a wristband mode, and the second working mode is a running mode, the first activity data is daily activity data, and the second activity data is running activity data.

The activity data collection method provided in this embodiment of this application may include: The wearable device 100 (namely, the device body 101) receives a user operation. The device body 101 starts the first-type sensor in response to a first operation of the user. The first-type sensor is configured to collect the first activity data (namely, the daily activity data). The device body 101 starts the second-type sensor in response to a second operation of the user. The second-type sensor is configured to collect the second activity data (namely, the running activity data).

In some embodiments, the first operation may be that the device body 101 is fastened to the watchband 102 (namely, the first carrier 102) shown in FIG. 2(*a*). The second operation may be that the device body 101 is fastened to the shoe buckle 103 (namely, the second carrier 103) shown in FIG. 3(*a*).

As shown in FIG. 4A, the device body 101 includes a switching circuit 430. The switching circuit 430 includes a detection contact 431 and a detection port 432. The watchband 102 and the shoe buckle 103 each include a metal contact. In this embodiment, the device body 101 may monitor or periodically detect a contact voltage of the detection port 432 of the switching circuit 430 in real time.

In one case, the device body 101 is fastened to the watchband 102 shown in FIG. 2(*a*), to obtain the wristband 200 shown in FIG. 2(*b*). In this case, the detection contact 431 of the switching circuit 430 is in contact with the metal contact of the watchband 102. The device body 101 may detect that the contact voltage of the detection port 432 is a first voltage value. In response to detecting that the contact voltage is the first voltage value, the device body 101 may start the first-type sensor to collect the daily activity data. In this case, the wearable device 100 works in the wristband mode.

In another case, the device body 101 is fastened to the shoe buckle 103 shown in FIG. 3(*a*), to obtain the motion sensing device 300 shown in FIG. 3(*b*). In this case, the detection contact 431 of the switching circuit 430 is in contact with the metal contact of the shoe buckle 103. The device body 101 may detect that the contact voltage of the detection port 432 is a second voltage value. In response to detecting that the contact voltage is the second voltage value, the device body 101 may start the second-type sensor to collect the running activity data. In this case, the wearable device 100 works in the running mode.

In another embodiment, the device body 101 further includes a first preset hardware switch or key. In this embodiment, the first operation and the second operation may be different operations performed by the user on the first preset hardware switch or key. For example, the first operation may be a click operation performed by the user on the first preset hardware switch or key. The second operation may be a double-click operation performed by the user on the first preset hardware switch or key.

Alternatively, the device body 101 further includes a display. The first operation and the second operation may be different operations performed by the user on a first preset button or option displayed on the display. For example, the first operation is a double-click operation performed by the user on the first preset button or option displayed on the display. The second operation is a long press operation performed by the user on the first preset button or option displayed on the display.

In a first implementation, the user fastens the device body 101 to the watchband 102, to obtain the wristband 200 shown in FIG. 2(*b*). Then, the user may perform the first operation on the preset hardware switch or key, the first preset button or option. The device body 101 may start the first-type sensor in response to the first operation to collect the daily activity data. In this case, the wearable device 100 works in the wristband mode.

The user fastens the device body 101 to the shoe buckle 103, to obtain the motion sensing device 300 shown in FIG. 3(*b*). Then, the user may perform the second operation on the preset hardware switch or key, the first preset button or option. The device body 101 may start the second-type sensor in response to the second operation to collect the running activity data. In this case, the wearable device 10 works in the running mode.

In a second implementation, as shown in FIG. 4A, the device body 101 includes the switching circuit 430. The switching circuit 430 includes the detection contact 431 and the detection port 432. The watchband 102 and the shoe buckle 103 each include the metal contact. In this embodiment, the device body 101 may monitor or periodically detect the contact voltage of the detection port 432 of the switching circuit 430 in real time.

In the second implementation, the user fastens the device body 101 to the watchband 102, to obtain the wristband 200 shown in FIG. 2(*b*). Then, the user may perform the first operation on the preset hardware switch or key, the first preset button or option. The detection contact 431 of the switching circuit 430 is in contact with the metal contact of the watchband 102 in response to the first operation. The device body 101 may detect that the contact voltage of the detection port 432 is the first voltage value. In response to detecting that the contact voltage is the first voltage value, the device body 101 may start the first-type sensor to collect the daily activity data. In this case, the wearable device 10 works in the wristband mode.

The user fastens the device body 101 to the shoe buckle 103, to obtain the motion sensing device 300 shown in FIG. 3(*b*). Then, the user may perform the second operation on the preset hardware switch or key, the first preset button or option. The detection contact 431 of the switching circuit 430 is in contact with the metal contact of the shoe buckle 103 in response to the second operation. The device body 101 may detect that the contact voltage of the detection port 432 is the second voltage value. In response to detecting that the contact voltage is the second voltage value, the device body 101 may start the second-type sensor to collect the running activity data. In this case, the wearable device 100 works in the running mode.

In some embodiments, the wearable device 100 may further present the daily activity data or the running activity data to the user. For example, the device body 101 may include the display. When the wearable device 100 works in the wristband mode, the device body 101 collects the daily activity data, and may display the daily activity data on the display. When the wearable device 100 works in the running mode, the device body 101 collects the running activity data, and may display the running activity data on the display. Alternatively, the device body 101 may display the daily activity data or the running activity data on the display in response to an operation of turning on the display by the user.

In some other embodiments, the wearable device 100 (namely, the device body 101) may establish a wireless connection to an electronic device, and send the daily activity data or the running activity data to the electronic device through the wireless connection, so that the electronic device presents the daily activity data or the running activity data to the user. A method for establishing the wireless connection between the device body 101 and the electronic device is not described herein in this embodiment of this application.

For example, the electronic device may be a device such as a mobile phone, a tablet computer, or a Bluetooth headset. Electronic devices such as the mobile phone and the tablet computer may display the daily activity data or the running activity data. The Bluetooth headset may play voice data obtained by converting the daily activity data or the running activity data.

It should be noted that, in an implementation, in a process of collecting the activity data, the device body 101 may send the collected activity data (for example, the daily activity data or the running activity data) in real time or periodically to the electronic device that establishes the wireless connection to the device body 101.

In another implementation, the device body 101 may send, in response to an end of an exercise, the activity data (for example, the daily activity data or the running activity data) collected in the exercise process to the electronic device that establishes the wireless connection to the device body 101. The device body 101 may include the hardware switch or key used to control the device body 101 to start and close the sensor. Alternatively, the display of the device body 101 may display the button or option used to control the device body 101 to start and close the sensor. In a process in which the device body 101 collects the activity data, if the device body 101 receives the click operation performed by the user on the hardware switch or key, the button or option, it may be determined that the exercise ends.

In another implementation, the electronic device may send a data request to the device body 101 through the wireless connection to the device body 101. After receiving the data request, the device body 101 may send the collected activity data (for example, the daily activity data or the running activity data) to the electronic device through the wireless connection.

For example, the wireless connection may be a short-distance wireless connection such as a Bluetooth connection, a Wi-Fi connection, or a near field communication (near field communication, NFC). Alternatively, the wireless connection may be a mobile communication connection.

In some embodiments, an app used to control the wearable device 100 may be installed in the electronic device. The device body 101 may send, through the wireless connection, the activity data collected by the device body 101 to the electronic device on which the app is installed. The electronic device presents the activity data on an interface of the app. Alternatively, the user may trigger, in the app, the electronic device to actively obtain, from the device body 101, the activity data collected by the device body 101.

In some other embodiments, the device body 101 may send, by using a cloud server, the collected activity data to the electronic device on which the app is installed. For example, the device body 101 may send the collected activity data to the cloud server in a process of collecting the activity data or in response to the end of the exercise. After starting the app, the electronic device on which the app is installed may send a data request to the cloud server. After receiving the data request, the cloud server may send the activity data to the electronic device. The electronic device may present the activity data on the interface of the app.

In some embodiments, after detecting the first operation or the second operation, the wearable device 100 may not first start the first-type sensor or the second-type sensor. Instead, the wearable device 100 starts the corresponding sensor only after receiving a first message sent by the electronic device. The first message is used to indicate the wearable device 100 to start to collect the activity data of the user. Specifically, after the device body 101 receives the first operation, the device body 101 starts the first-type sensor in response to receiving the first message sent by the electronic device. After the device body 101 receives the second operation, the device body 101 starts the second-type sensor in response to receiving the first message sent by the electronic device.

For example, the interface of the app displayed by the electronic device may include a "Start exercise" button. The "Start exercise" button is used to trigger the wearable device 100 to start to collect the activity data of the user. The electronic device may receive a click operation performed by the user on the "Start exercise" button. In response to the click operation performed by the user on the "Start exercise" button, the electronic device may send the first message to the device body 101 through the wireless connection. After receiving the first message, the device body 101 may start the first-type sensor or the second-type sensor.

In a process of using the wearable device 10, the wearable device 100 may switch from the wristband mode to the running mode in response to the user operation, or switch from the running mode to the wristband mode in response to the user operation. In an embodiment of this application, a working procedure of a wearable device 10 is described by using an example in which a first operation is that a device body 101 is fastened to a watchband 102, a second operation is that the device body 101 is fastened to a shoe buckle 103, and the electronic device is a mobile phone 500.

The device body 101 may detect a contact voltage in real time (that is, perform S501). After a user fastens the device body 101 to the shoe buckle 103, the device body 101 may detect that the contact voltage is a second voltage value, and determine that the wearable device 100 is in a running mode (that is, perform S502). The device body 101 may establish a Bluetooth connection to the mobile phone (that is, perform S500). Optionally, after S502, the device body 101 may further notify, through the Bluetooth connection to the mobile phone, the mobile phone that the wearable device 100 is in the running mode (that is, perform S503). For example, the device body 101 may send a first notification message to the mobile phone through the Bluetooth connection to the mobile phone. The first notification message is used to indicate that the wearable device 100 is in the running mode. Correspondingly, after receiving the first notification message, the mobile phone may prompt, on an interface of an app, the user that the wearable device 100 is in the running mode. For example, the interface of the app may include prompt information such as "Running mode" or "Currently in a running mode".

With reference to the foregoing example, the interface of the app displayed by the mobile phone may include the "Start exercise" button. The user may click the "Start exercise" button on the interface of the app, to control the wearable device 100 to start to collect activity data of the user, that is, start a sensor. The mobile phone may receive the click operation performed by the user on the "Start exercise" button on the interface of the app (that is, perform S505). In response to the click operation performed by the user on the "Start exercise" button, the mobile phone may send a first message to the device body 101 through the Bluetooth connection to the device body 101 (that is, perform S506). The first message is used to indicate the device body 101 to start to collect the activity data of the user. In response to the first message, because the wearable device 100 is in the running mode, the device body 101 may start a second-type sensor to collect running activity data (that is, perform S507). The device body 101 may further send the collected running activity data to the mobile phone (that is, perform S508). In this way, the mobile phone may display the running activity data on the interface of the app (that is, perform S509). For a moment and a method for sending the collected running activity data to the mobile phone by the device body 101, refer to the descriptions in the foregoing embodiment. Details are not described herein again in this embodiment of this application.

The user wants to use different functions of the wearable device 100 at different time or in different scenarios. For example, when the device body 101 is fastened to the shoe buckle 103, the user may remove the device body 101 from the shoe buckle 103, and then fasten the device body 101 to the watchband 102, so as to use the wearable device 100 as a wristband. In this case, the device body 101 may detect that the contact voltage is a first voltage value, and determine that the wearable device 100 is in a wristband mode (that is, perform S510). Optionally, after S510, the device body 101 may further notify, through the Bluetooth connection to the mobile phone, the mobile phone that the wearable device 100 is in the wristband mode (that is, perform S511). For example, the device body 101 may send a second notification message to the mobile phone through the Bluetooth connection to the mobile phone. The second notification message is used to indicate that the wearable device 100 is in the wristband mode. Correspondingly, after receiving the second notification message, the mobile phone may prompt, on the interface of the app, the user that the wearable device 10 is in the wristband mode. For example, the interface of the app may include prompt information such as "Wristband mode" or "Currently in a wristband mode".

The device body 101 switches a working mode. For example, after the working mode of the device body 101 is switched from the "Running mode" to the "Wristband mode", the "Start exercise" button may be displayed on the interface of the app displayed on the mobile phone. The mobile phone may receive the click operation performed by the user on the "Start exercise" button on the interface of the app (that is, perform S513). In response to the click operation performed by the user on the "Start exercise" button, the mobile phone may send the first message to the device body 101 through the Bluetooth connection to the device body 101 (that is, perform S514). The first message is used to indicate the device body 101 to start to collect the activity data of the user. In response to the first message, because the wearable device 100 is in the wristband mode, the device body 101 may start a first-type sensor to collect daily activity data (that is, perform S515). The device body 101 may further send the collected daily activity data to the mobile phone (that is, perform S516). In this way, the mobile phone may display the daily activity data on the interface of the app (that is, perform S517). For a moment and a method for sending the collected daily activity data to the mobile phone by the device body 101, refer to the descriptions in the foregoing embodiment. Details are not described herein again in this embodiment of this application.

Generally, one electronic device includes one MAC address. The user may control the electronic device to establish Bluetooth connections to different electronic devices at different time. For example, the user may control the electronic device to establish a Bluetooth connection to a mobile phone A, control the electronic device to disconnect the Bluetooth connection to the mobile phone A, and then, control the electronic device to establish a Bluetooth connection to a tablet computer B. In this way, the mobile phone A may store a MAC address of the electronic device. The tablet computer B may also store the MAC address of the electronic device. After the two Bluetooth devices (for example, the electronic device and the mobile phone A) store the MAC address of the electronic device, when distances between the electronic device and the two Bluetooth devices are less than a specific value, Bluetooth connections may be automatically established.

However, in some scenarios, user experience may be affected because the electronic device automatically establishes a Bluetooth connection to another electronic device. For example, with reference to the foregoing example, the electronic device has established a Bluetooth connection to both the mobile phone A and the tablet computer B, and both the mobile phone A and the tablet computer B store the MAC address of the electronic device. Bluetooth functions of the electronic device, the mobile phone A, and the tablet computer B are all started, and the mobile phone A and the tablet computer B are placed together (that is, a distance between the mobile phone A and the tablet computer B is relatively short).

It is assumed that the electronic device (for example, a Bluetooth headset) establishes a Bluetooth connection to the mobile phone A. The electronic device is held by the user, and is listening to, through the Bluetooth connection to the mobile phone A, music played on the mobile phone A. However, because the user moves, a distance between the mobile phone A and the electronic device is relatively long. As a result, the Bluetooth connection between the mobile phone A and the electronic device is disconnected. When the user holds the electronic device to approach the mobile phone A again, the electronic device may automatically establish a Bluetooth connection to the tablet computer B, instead of automatically establishing the Bluetooth connection to the mobile phone A. In this case, the user needs to manually control the mobile phone A to establish the Bluetooth connection to the electronic device, so that the user can continue to listen to, by using the electronic device, the music played on the mobile phone A.

For the problem, an embodiment of this application provides an electronic device. The electronic device may include two or less than two MACs. For example, the electronic device includes two MAC addresses. For example, the electronic device includes a first MAC address (namely, a MAC address 1) and a second MAC address (namely, a MAC address 2). The electronic device may establish Bluetooth connections to a plurality of other electronic devices by using the two MAC addresses. For example, in the foregoing example, the electronic device may establish the wireless connection to the mobile phone A by using the MAC address 1, and establish the wireless connection to the tablet computer B by using the MAC address 2. In this way, when a user holds the electronic device to approach the mobile phone A again, the electronic device may not automatically establish the Bluetooth connection to the tablet computer B, but automatically establish the Bluetooth connection to the mobile phone A. Therefore, the user does not need to manually control the electronic device to establish the Bluetooth connection to the mobile phone A.

The electronic device may receive a third operation of the user, and use the MAC address 1 as the MAC address of the electronic device. In this case, the electronic device may broadcast a message including the MAC address 1, so that the another electronic device may establish a Bluetooth connection to the electronic device based on the MAC address 1 in the received message.

The electronic device may receive a fourth operation of the user, and use the MAC address 2 as the MAC address of the electronic device. In this case, the electronic device may broadcast a message including the MAC address 2, so that the another electronic device may establish a Bluetooth connection to the electronic device based on the MAC address 2 in the received message.

For example, the electronic device may be a portable computer (for example, a mobile phone), a notebook computer, a personal computer (personal computer, PC), a wearable device (for example, a smartwatch), a tablet computer, an augmented reality (augmented reality, AR)/a virtual reality (virtual reality, VR) device, and an in-vehicle computer. A specific form of the electronic device is not specifically limited in the following embodiments.

In an implementation, the electronic device may further include a second preset hardware switch or key (namely, a preset switch). The second preset hardware switch or key is used to control the electronic device to use the MAC address 1 or the MAC address 2. The third operation and the fourth operation may be different operations performed by the user on the second preset hardware switch or key.

Figure 6:
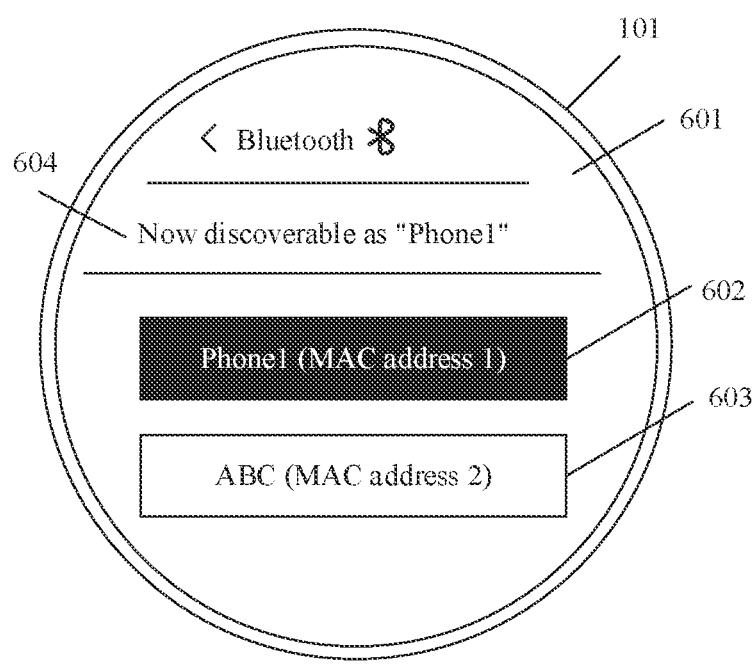
FIG. 6 is a schematic diagram of an example of a Bluetooth interface according to an embodiment of this application.

In another implementation, the electronic device may further include a display. The third operation is a selection operation performed by the user on an option corresponding to the MAC address 1. The fourth operation is a selection operation performed by the user on an option corresponding to the MAC address 2. For example, the electronic device is the wearable device 100. FIG. 6 shows a Bluetooth setting interface 601 of a device body 101 of the wearable device 100. The wearable device 100 may receive a click operation (namely, a fifth operation) performed by the user on a "Bluetooth" option of a "Settings" application. The Bluetooth setting interface 601 is displayed in response to the fifth operation. The Bluetooth setting interface 601 includes the option corresponding to the MAC address 1, for example, a "Phone1" option 602, and the option corresponding to the MAC address 2, for example, an "ABC" option 603. The third operation may be a click operation (for example, a click operation) performed by the user on the "Phone1" option 602. The fourth operation may be a click operation (for example, a click operation) performed by the user on the "ABC" option 603. The Bluetooth setting interface 601 is a Bluetooth setting interface when the device body 101 uses the MAC address 1 after the "Phone1" option 602 is clicked by the user (the "Phone1" option 602 is marked black).

Phone1 is a name set by the user when the device body 101 uses the MAC address 1. ABC is a name set by the user when the device body 101 uses the MAC address 2. As shown in FIG. 6, the Bluetooth setting interface 601 may further include prompt information 601, for example, Now discoverable as "Phone1". The prompt information 601 is used to indicate that the device body 101 currently uses the MAC address 1. The device body 101 may broadcast the message including the MAC address 1. The another electronic device (for example, the mobile phone A or the tablet computer B) whose Bluetooth function is started may receive the message that is broadcast by the device body 101 and that includes the MAC address 1.

Figure 7:
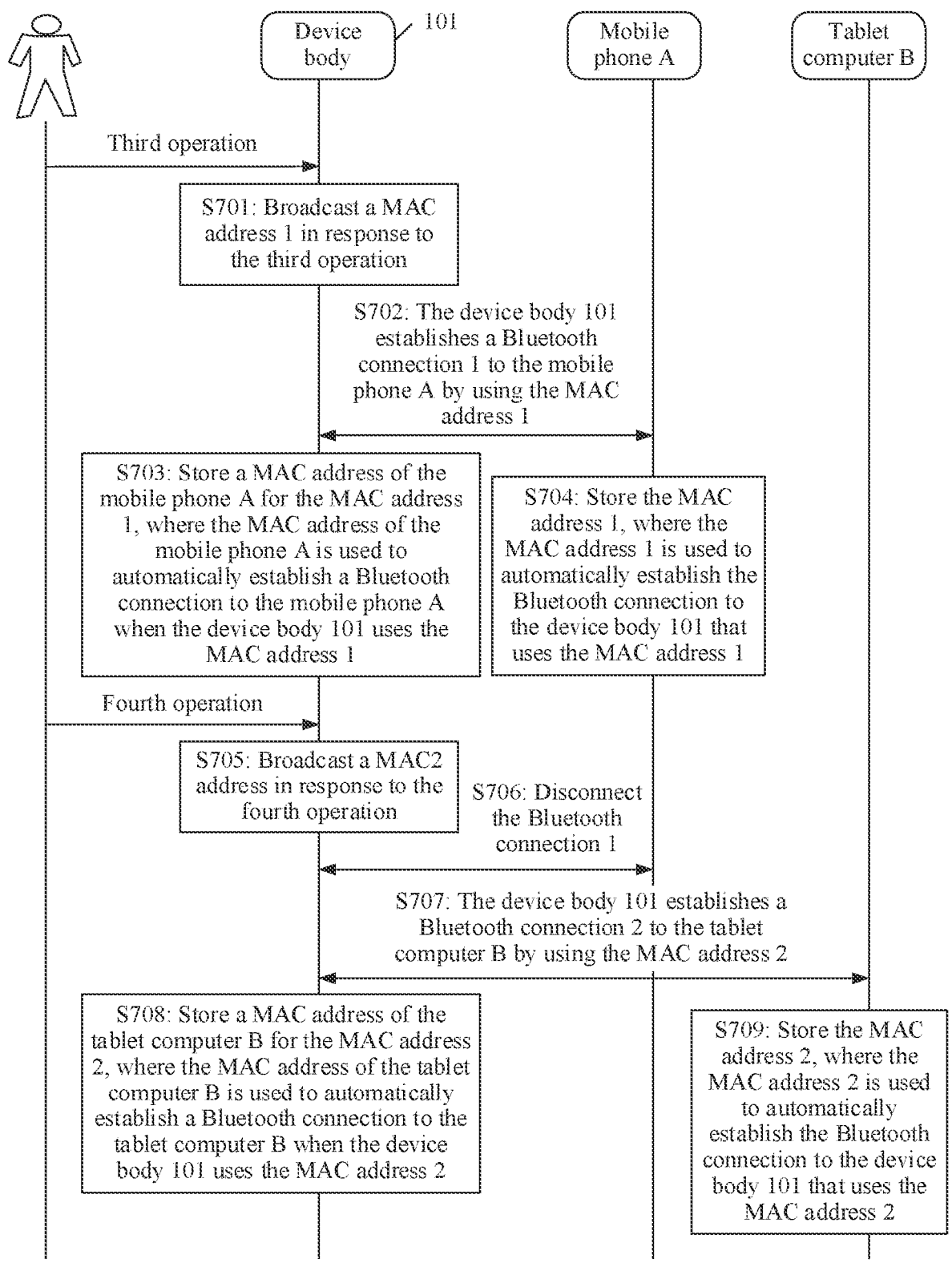
FIG. 7 is a flowchart of another activity data collection method according to an embodiment of this application.

Referring to FIG. 7, in an embodiment of this application, a process in which the electronic device establishes Bluetooth connections to other electronic devices by using a MAC address 1 or a MAC address 2 is described by using an example in which the electronic device is a wearable device 100 (namely, a device body 101).

The device body 101 may receive a third operation of a user. In response to the third operation, the device body 101 may broadcast the MAC address 1 (that is, broadcast a message including the MAC address 1), that is, perform S701. Therefore, the other electronic devices (for example, a mobile phone A and a tablet computer B) whose Bluetooth functions are started may receive the message including the MAC address 1. In response to the message including the MAC address 1, both the mobile phone A and the tablet computer B may display on Bluetooth search interfaces of the mobile phone A and the tablet computer B, the MAC address 1, or a name (for example, Phone1) set by a user when the device body 101 uses the MAC address 1.

For example, it is assumed that a MAC address of the mobile phone A is a MAC address A, a name set by the user for the mobile phone A is shoujiA, a MAC address of the tablet computer B is a MAC address B. and a name set by the user for the tablet computer B is pingbanB.

Figure 7A:
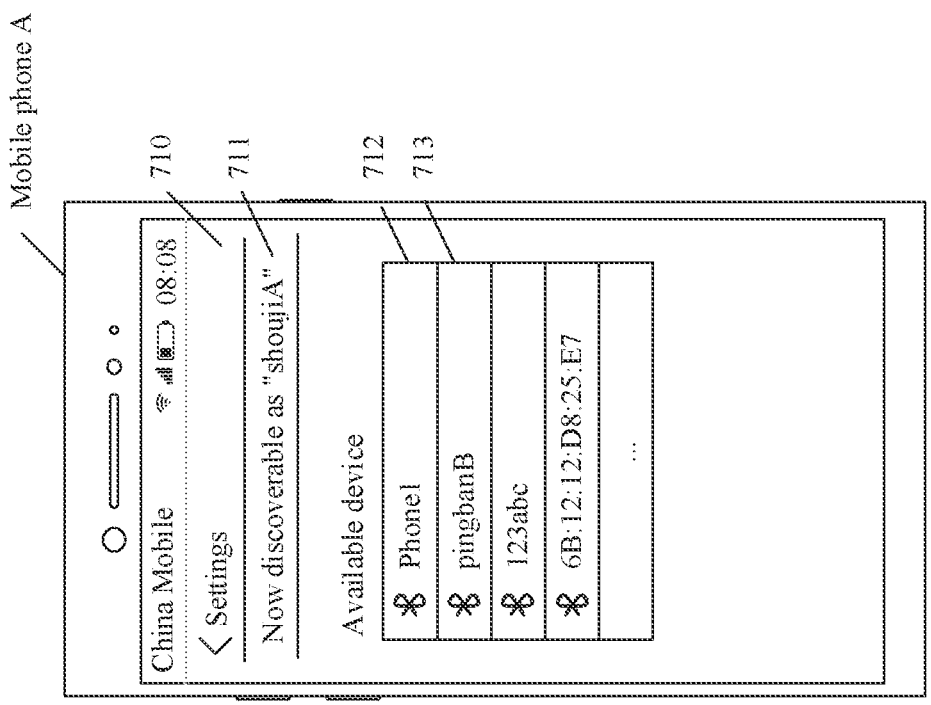
FIG. 7A(a) and FIG. 7A(b) are a schematic diagram of an example of another Bluetooth interface according to an embodiment of this application.
Figure 7A:
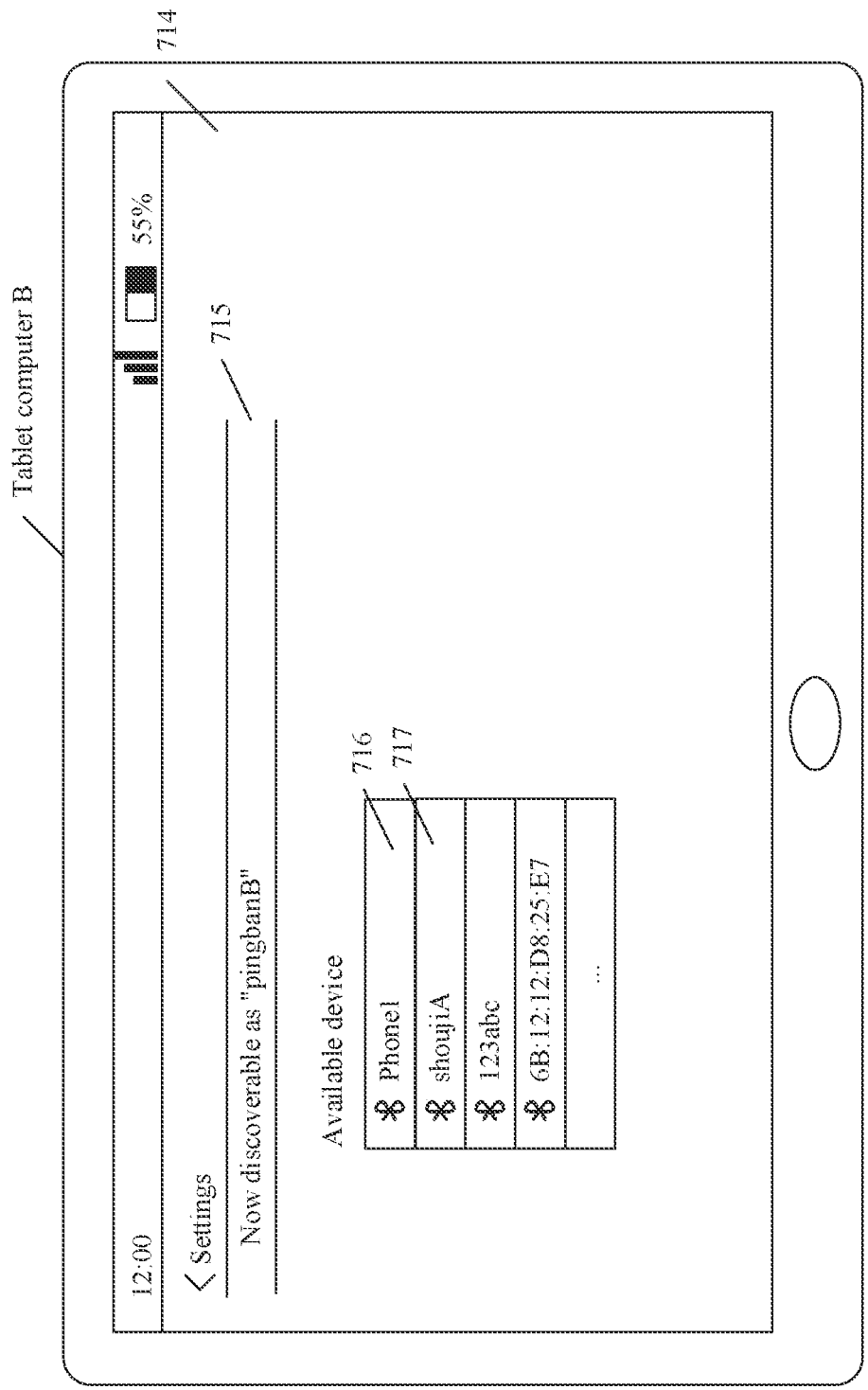

As shown in FIG. 7A(a), the mobile phone A may display a Bluetooth search interface 710. The Bluetooth search interface 710 includes prompt information 711, for example, Now discoverable as "shoujiA". The Bluetooth search interface 710 further includes options corresponding to a plurality of available devices. The plurality of available devices are devices whose Bluetooth broadcast signals can be found by the mobile phone A. For example, the Bluetooth search interface 710 includes a "pingbanB" option 713, and a "Phone1" option 712. The "pingbanB" option 713 corresponds to the tablet computer B, and indicates that the mobile phone A receives a Bluetooth broadcast signal that is sent by the tablet computer B and that includes the MAC address B. The "Phone1" option 712 corresponds to the device body 101 that uses the MAC address 1, and indicates that the mobile phone A receives a Bluetooth broadcast signal that is sent by the device body 101 and that includes the MAC address 1.

As shown in FIG. 7A(b), the tablet computer B may display a Bluetooth search interface 714. The Bluetooth search interface 714 includes prompt information 715, for example, Now discoverable as "pingbanB". The Bluetooth search interface 714 further includes options corresponding to a plurality of available devices. The plurality of available devices are devices whose Bluetooth broadcast signals can be found by the tablet computer B. For example, the Bluetooth search interface 714 includes a "shoujiA" option 717, and a "Phone1" option 716. The "shoujiA" option 717 corresponds to the mobile phone A, and indicates that the tablet computer B receives a Bluetooth broadcast signal that is sent by the mobile phone A and that includes the MAC address A. The "Phone1" option 716 corresponds to the device body 101 that uses the MAC address 1, and indicates that the tablet computer B receives a Bluetooth broadcast signal that is sent by the device body 101 and that includes the MAC address 1.

Figure 7B:
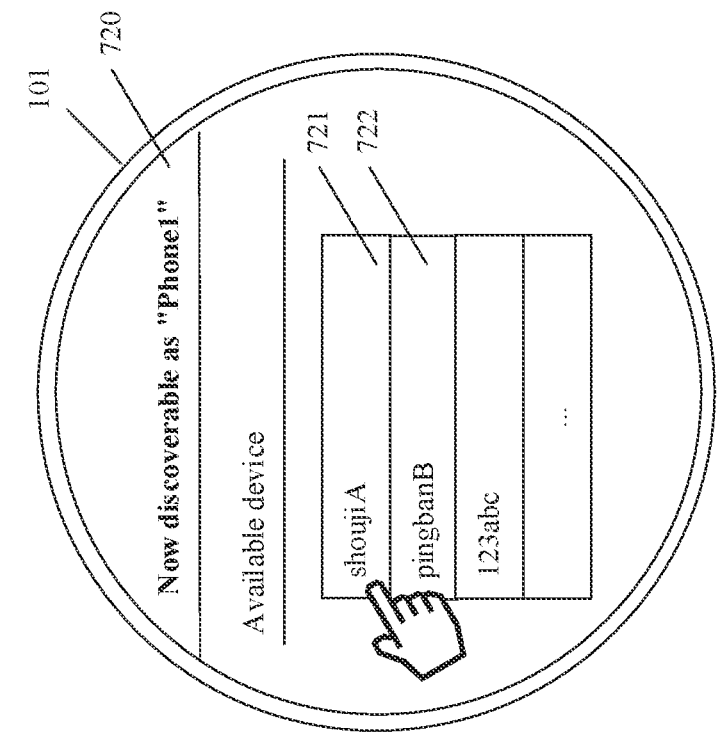
FIG. 7B(a) and FIG. 7B(b) are a schematic diagram of an example of another Bluetooth interface according to an embodiment of this application.
Figure 7B:
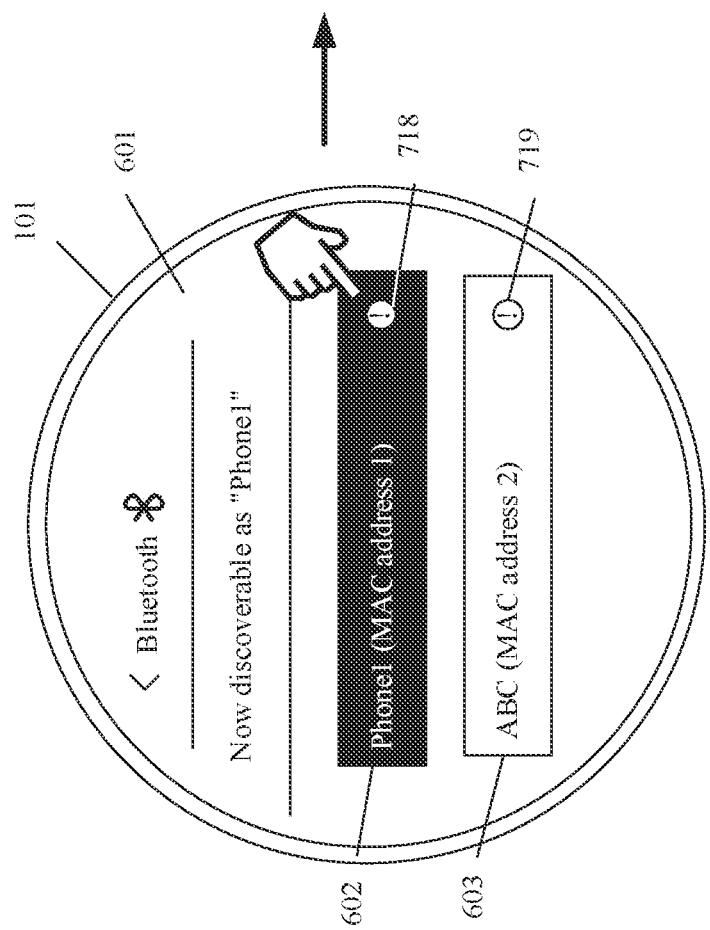

It is assumed that when the device body 101 uses the MAC address 1, the user controls the device body 101 to establish a Bluetooth connection to the mobile phone A. For example, as shown in FIG. 7B(a), a Bluetooth option 602 includes an option (which may be referred to as a Details option) 718, and a Bluetooth option 603 includes an option (which may be referred to as a Details option) 719. In response to a click operation of the user on the option 718, the device body 101 may display a Bluetooth search interface 720 shown in FIG. 7B(b). The Bluetooth search interface 720 includes: a "shoujiA" option 721, a "pingbanB" option 722, and the like. The "shoujiA" option 721 corresponds to the mobile phone A, and indicates that the device body 101 receives the Bluetooth broadcast signal that is sent by the mobile phone A and that includes the MAC address A. The "pingbanB" option 722 corresponds to the tablet computer B. and indicates that the device body 101 receives the Bluetooth broadcast signal that is sent by the tablet computer B and that includes the MAC address B. The device body 101 may receive a click operation performed by the user on the "shoujiA" option 721, and request, by using the MAC address 1, to establish the Bluetooth connection to the mobile phone A. As shown in FIG. 7, the device body 101 may establish a Bluetooth connection 1 to the mobile phone A by using the MAC address 1 (that is, perform S702). For a method for establishing the Bluetooth connection 1 between the mobile phone A and the device body 101, refer to descriptions in a conventional technology. Details are not described herein in this embodiment of this application.

After the device body 101 establishes the Bluetooth connection 1 to the mobile phone A by using the MAC address 1, the device body 101 may store the MAC address of the mobile phone A for the MAC address 1 (that is, perform S703). The MAC address of the mobile phone A is used to automatically establish the Bluetooth connection to the mobile phone A when the device body 101 uses the MAC address 1. For example, after the device body 101 establishes the Bluetooth connection 1 to the mobile phone A by using the MAC address 1, as shown in FIG. 7C(a), a connection identifier 723 may be displayed in the "shoujiA" option 721. The connection identifier 723 is used to indicate that the device body 101 has established the Bluetooth connection to the mobile phone A. Optionally, the Bluetooth search interface shown in FIG. 7C(a) may further include a "Trusted device" option 724. In response to a click operation performed by the user on the "Trusted device" option 724, the device body 101 may display a trusted device interface 725 shown in FIG. 7C(b). The trusted device interface 725 includes a "shoujiA" option 726. The trusted device interface 725 includes the "shoujiA" option 726, which is used to indicate that the device body 101 has stored the MAC address of the mobile phone A for the MAC address 1. When the device body 101 uses the MAC address 1, the device body 101 may automatically establish the Bluetooth connection to the mobile phone A. Likewise, the mobile phone A may also store the MAC address 1 (that is, perform S704). The MAC address 1 stored in the mobile phone A is used to automatically establish the Bluetooth connection to the device body 101 that uses the MAC address 1.

After the device body 101 establishes the Bluetooth connection 1 to the mobile phone A by using the MAC address 1, the device body 101 may receive a fourth operation of the user. For example, the fourth operation may be a click operation performed by the user on an "ABC" Bluetooth option 603 shown in FIG. 7D(a). In response to the fourth operation, the device body 101 may broadcast the MAC address 2 (that is, broadcast a message including the MAC address 2), that is, perform S705. In this case, because the device body 101 uses the MAC address 2 instead of the MAC address 1, the Bluetooth connection 1 between the device body 101 and the mobile phone A is disconnected (that is, S706 is performed).

Therefore, the other electronic device (for example, the mobile phone A and the tablet computer B) whose Bluetooth functions are started may receive the message including the MAC address 2. In response to the message including the MAC address 2, both the mobile phone A and the tablet computer B may display on Bluetooth search interfaces of the mobile phone A and the tablet computer B, the MAC address 2, or a name (for example, ABC) set by the user when the device body 101 uses the MAC address 2.

Figure 7F:
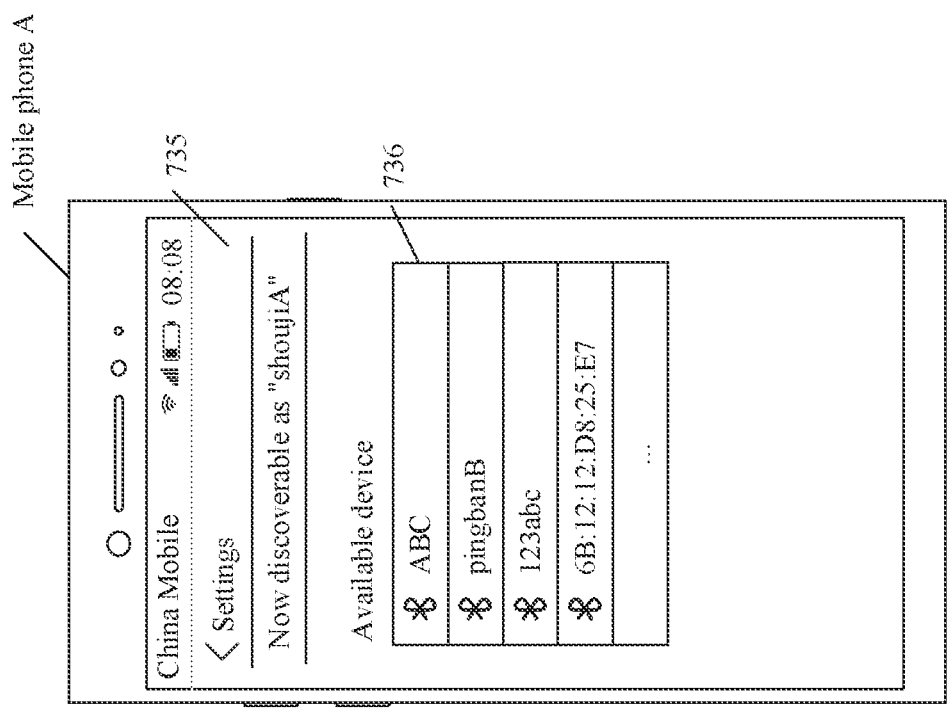
FIG. 7F(a) and FIG. 7F(b) are a schematic diagram of an example of another Bluetooth interface according to an embodiment of this application.
Figure 7F:
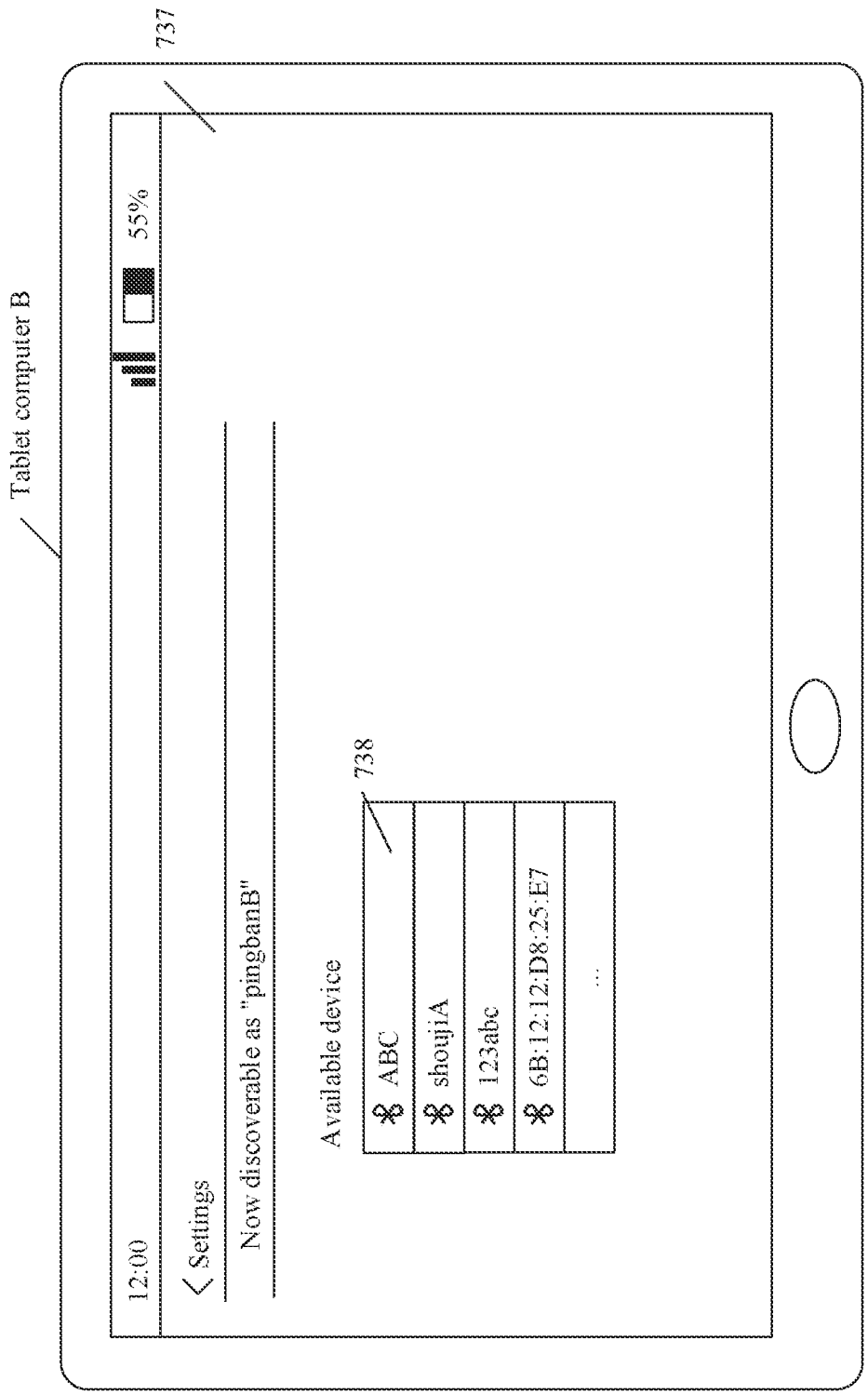

As shown in FIG. 7F(a), the mobile phone A may display a Bluetooth search interface 735. The Bluetooth search interface 735 includes a "pingbanB" option, an "ABC" option 736, and the like. The "pingbanB" option corresponds to the tablet computer B. and indicates that the mobile phone A receives the Bluetooth broadcast signal that is sent by the tablet computer B and that includes the MAC address B. The "ABC" option 736 corresponds to the device body 101 that uses the MAC address 2, and indicates that the mobile phone A receives the Bluetooth broadcast signal that is sent by the device body 101 and that includes the MAC address 2.

As shown in FIG. 7F(b), the tablet computer B may display a Bluetooth search interface 737. The Bluetooth search interface 737 includes a "shoujiA" option, an "ABC" option 738, and the like. The "shoujiA" option corresponds to the mobile phone A, and indicates that the tablet computer B receives the Bluetooth broadcast signal that is sent by the mobile phone A and that includes the MAC address A. The "ABC" option 738 corresponds to the device body 101 that uses the MAC address 2, and indicates that the tablet computer B receives the Bluetooth broadcast signal that is sent by the device body 101 and that includes the MAC address 2.

It is assumed that when the device body 101 uses the MAC address 2, the user controls the device body 101 to establish a Bluetooth connection to the tablet computer B. For example, as shown in FIG. 7D(b), in response to a click operation performed by the user on the option 719, the device body 101 may display a Bluetooth search interface 728 shown in FIG. 7D(c). The Bluetooth search interface 728 includes: a "shoujiA" option 729, a "pingbanB" option 730, and the like. The "shoujiA" option 729 corresponds to the mobile phone A. and indicates that the device body 101 receives the Bluetooth broadcast signal that is sent by the mobile phone A and that includes the MAC address A. The "pingbanB" option 738 corresponds to the tablet computer B, and indicates that the device body 101 receives the Bluetooth broadcast signal that is sent by the tablet computer B and that includes the MAC address B. The device body 101 may receive a click operation performed by the user on the "pingbanB" option 738, and request, by using the MAC address 2, to establish the Bluetooth connection to the tablet computer B. As shown in FIG. 7, the device body 101 may establish a Bluetooth connection 2 to the tablet computer B by using the MAC address 2 (that is, perform S707). Then, the device body 101 may store the MAC address of the tablet computer B for the MAC address 2 (that is, perform S708). The MAC address of the tablet computer B is used to automatically establish the Bluetooth connection to the tablet computer B when the device body 101 uses the MAC address 2. The tablet computer B may also store the MAC address 2 (that is, perform S709). The MAC address 2 stored in the tablet computer B is used to automatically establish the Bluetooth connection to the device body 101 that uses the MAC address 2.

It may be understood that the device body 101 stores the MAC address of the mobile phone A for the MAC address 1 (for example, S703), and the device body 101 stores the MAC address of the tablet computer B for the MAC address 2 (for example, S708). Therefore, when the device body 101 uses the MAC address 1 in response to the third operation, the device body 101 may automatically establish the Bluetooth connection to the mobile phone A. When the device body 101 uses the MAC address 2 again in response to the fourth operation, the device body 101 may automatically establish the Bluetooth connection to the tablet computer B. For example, after the device body 101 establishes the Bluetooth connection 2 to the mobile phone A by using the MAC address 2, as shown in FIG. 7E(a), a connection identifier 731 may be displayed in the "pingbanB" option 730. The connection identifier 731 is used to indicate that the device body 101 has established the Bluetooth connection to the tablet computer B. Optionally, the Bluetooth search interface shown in FIG. 7E(a) may further include a "Trusted device" option 732. In response to a click operation performed by the user on the "Trusted device" option 732, the device body 101 may display a trusted device interface 733 shown in FIG. 7E(b). The trusted device interface 733 includes a "pingbanB" option 730. The trusted device interface 725 includes the "pingbanB" option 730, which is used to indicate that the device body 101 has stored the MAC address of the tablet computer B for the MAC address 2. When the device body 101 uses the MAC address 2, the device body 101 may automatically establish the Bluetooth connection to the tablet computer B. Likewise, the tablet computer B may also store the MAC address 2 (that is, perform S709). The MAC address 2 stored in the tablet computer B is used to automatically establish the Bluetooth connection to the device body 101 that uses the MAC address 2.

In some embodiments, when the device body 101 is in a running mode, to facilitate the user to view, at any time in a running process, running activity data collected by the device body 101, the user may control the device body 101 to establish a Bluetooth connection to an electronic device that can be viewed by the user at any time in the running process, such as a smartwatch or a smart wristband. In this way, the device body 101 may send the running activity data to the electronic device such as the smart watch or the smart wristband through the Bluetooth connection, so that the user can view the running activity data at any time in the running process. In other words, the tablet computer B in this embodiment may be replaced with the electronic device such as the smart watch or smart wristband.

The electronic device (for example, the wearable device 100) provided in this embodiment of this application includes two MAC addresses. The electronic device may establish Bluetooth connections to different other electronic devices by using different MACs. This can reduce a possibility of a misconnection caused by an automatic connection between the electronic device and the another electronic device.

In some embodiments, a working mode of the wearable device 100 may one-to-one correspond to a MAC address of the wearable device 100. For example, when the wearable device 100 is in a wristband mode, the MAC address 2 is used. When the wearable device 100 is in a running mode, the MAC address 1 is used. In this embodiment, the third operation is the same as the foregoing first operation, and the fourth operation is the same as the foregoing second operation.

Figure 8A:
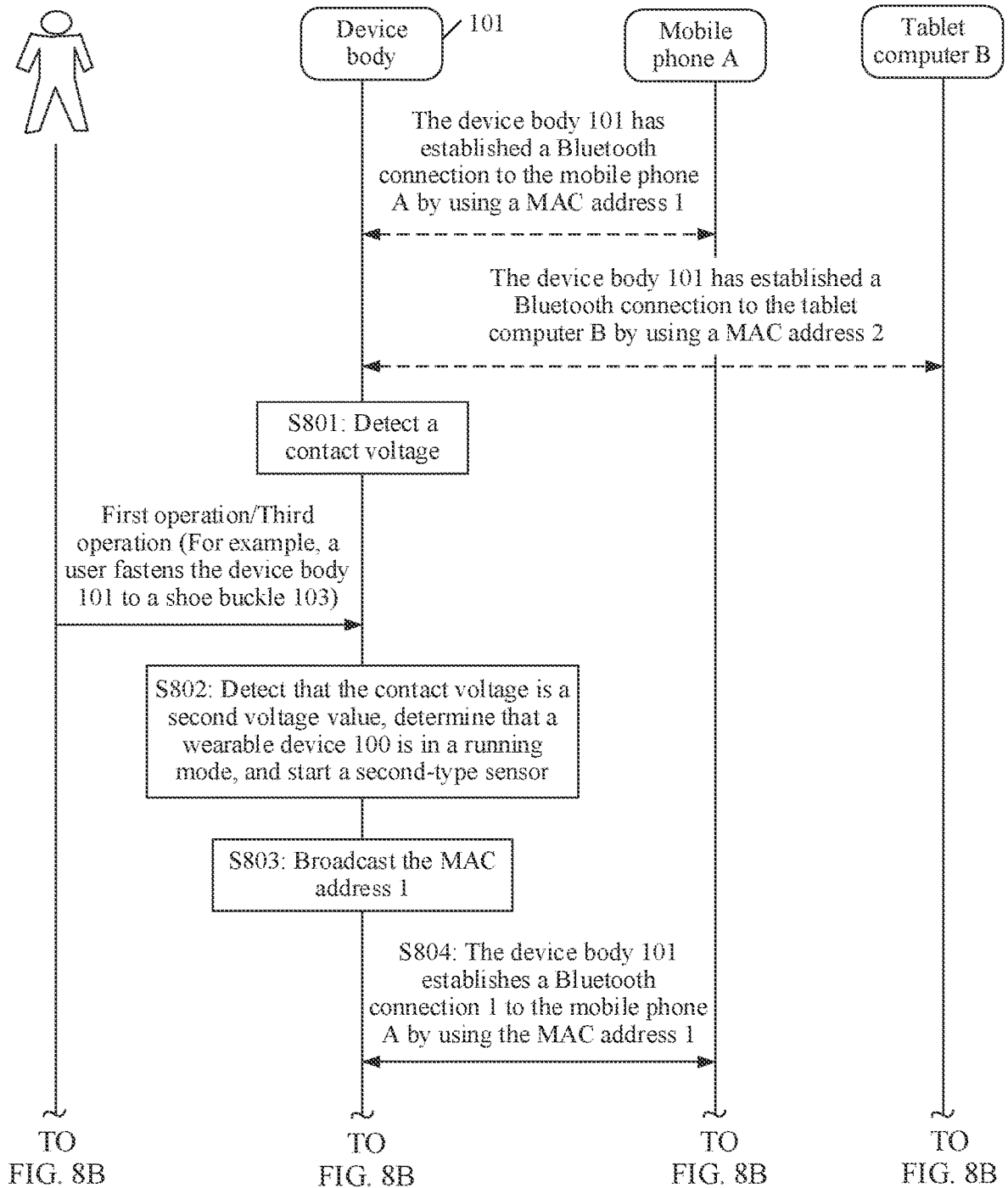
FIG. 8A and FIG. 8B are a flowchart of another activity data collection method according to an embodiment of this application.
Figure 8B:
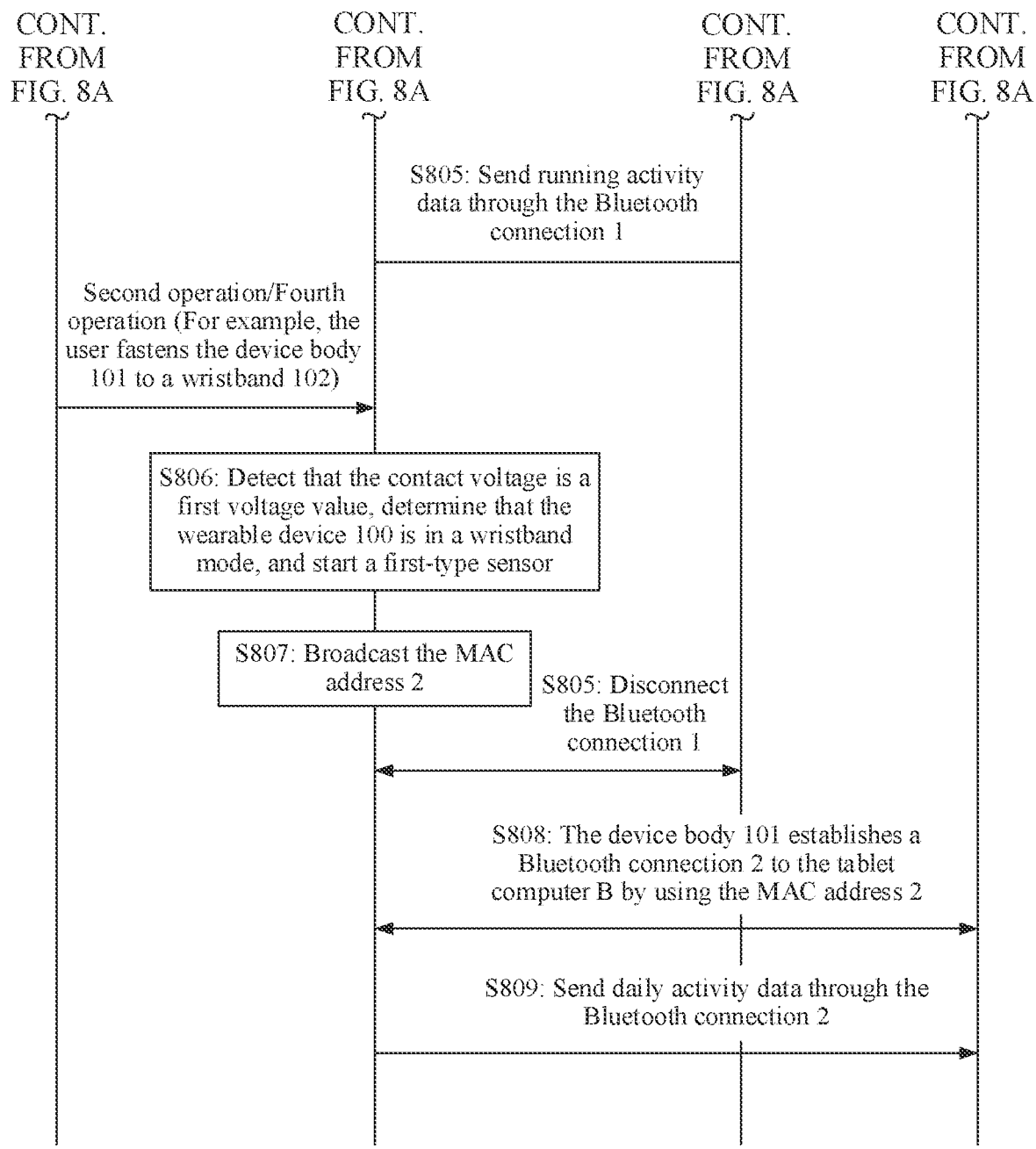

Referring to FIG. 8A and FIG. 8B, a process in which a wearable device 100 uses a MAC address 2 in a wristband mode and uses a MAC address 1 in a running mode to establish Bluetooth connections to other electronic devices is described in an embodiment of this application.

As shown in FIG. 8A and FIG. 8B, it is assumed that a device body 101 has established a Bluetooth connection to a mobile phone A by using the MAC address 1, and has established a Bluetooth connection to a tablet computer B by using the MAC address 2. The device body 101 may detect a contact voltage in real time (that is, perform S801).

The device body 101 may receive a third operation (that is, a first operation, for example, a user may fasten the device body 101 to a shoe buckle 103) of the user. In response to the third operation, and in response to the third operation, the device body 101 may detect that the contact voltage is a second voltage value, determine that the wearable device 100 is in the running mode, and start a second-type sensor (that is, perform S802). In addition, the device body 101 may broadcast the MAC address 1 (that is, broadcast a message including the MAC address 1), that is, perform S803. In this way, after receiving the message including the MAC address 1, the mobile phone A may automatically establish a Bluetooth connection 1 to the device body 101 (that is, perform S804). Then, the device body 101 may send, to the mobile phone A through the Bluetooth connection 1, running activity data collected by the second-type sensor (that is, perform S805).

The device body 101 may receive a fourth operation (that is, a second operation, for example, the user may fasten the device body 101 to a watchband 102) of the user. In response to the fourth operation, the device body 101 may detect that the contact voltage is a first voltage value, determine that the wearable device 100 is in the wristband mode, and start a first-type sensor (that is, perform S806). In addition, the device body 101 may broadcast the MAC address 2 (that is, broadcast a message including the MAC address 2), that is, perform S807. In this way, after receiving the message including the MAC address 2, the tablet computer B may automatically establish a Bluetooth connection 2 to the device body 101 (that is, perform S808). In addition, after the device body 101 uses the MAC address 2, the Bluetooth connection 1 between the device body 101 and the mobile phone A is disconnected (that is, S805 is performed). After the Bluetooth connection 2 is established, the device body 101 may send, to the tablet computer B through the Bluetooth connection 2, daily activity data collected by the first-type sensor (that is, perform S809).

In this embodiment of this application, the wearable device 100 (namely, the device body 101) includes a plurality of MAC addresses. When the wearable device 100 (namely, the device body 101) is in different working modes, different MAC addresses may be used. For example, the wearable device 100 includes two MAC addresses. For example, w % ben the wearable device 100 is in the wristband mode, the MAC address 2 is used. When the wearable device 100 is in the running mode, the MAC address 1 is used. In addition, the wearable device 100 may establish Bluetooth connections to different electronic devices by using the different MAC. In conclusion, when the wearable device 100 is in the different working modes, the wearable device 100 may establish the Bluetooth connections to the different electronic devices by using the different MAC addresses. This can reduce a possibility of a misconnection caused by an automatic connection between the wearable device 100 and another electronic device.

It may be understood that, to implement the foregoing functions, the wearable device 100 includes corresponding hardware structures and/or software modules for performing the functions. A person skilled in the art should be easily aware that, in combination with units and algorithm steps of the examples described in the embodiments disclosed in this specification, the embodiments of this application may be implemented by hardware or a combination of hardware and computer software. Whether a function is performed by hardware or hardware driven by computer software depends on particular applications and design constraints of the technical solutions. A person skilled in the art may use different methods to implement the described functions for each particular application, but it should not be considered that the implementation goes beyond the scope of the embodiments of this application.

In the embodiments of this application, the wearable device 100 may be divided into function modules based on the foregoing method examples. For example, each function module may be obtained through division based on each corresponding function, or two or more functions may be integrated into one processing module. The integrated module may be implemented in a form of hardware, or may be implemented in a form of a software functional module. It should be noted that, in this embodiment of this application, division into the modules is an example, and is merely a logical function division. In actual implementation, another division manner may be used.

An embodiment of this application further provides a wearable device. The wearable device includes a first carrier, a second carrier, and a device body. The device body includes a first-type sensor and a second-type sensor. For a structure of the device body, refer to the structure of the device body 101 shown in FIG. 4A. For example, the first carrier may be the watchband 102 shown in FIG. 1, FIG. 2(*a*) and FIG. 2(*b*), or FIG. 3(*a*) and FIG. 3(*b*). The second carrier may be the shoe buckle 103 shown in FIG. 1, FIG. 2(*a*) and FIG. 2(*b*), or FIG. 3(*a*) and FIG. 3(*b*). A memory of the device body may store one or more computer programs. The one or more computer programs include instructions. When a processor of the device body executes the instructions, the device body 101 may perform functions or steps performed by the device body 101 or the wearable device 100 in the description of the foregoing method embodiments.

Further, a wireless communications module of the device body is provided with at least two MAC addresses. The at least two MAC addresses may include a first MAC address (for example, the foregoing MAC address 1) and a second MAC address (for example, the foregoing MAC address 2).

An embodiment of this application further provides a computer storage medium. The computer storage medium includes computer instructions. When the computer instructions are run on the foregoing wearable device, the wearable device is enabled to perform functions or steps performed by the device body 101 or the wearable device 100 in the description of the foregoing method embodiments.

An embodiment of this application further provides a computer program product. When the computer program product runs on a computer, the computer is enabled to perform functions or steps performed by the device body 101 or the wearable device 100 in the description of the foregoing method embodiments.

An embodiment of this application further provides an electronic device. The electronic device may be the foregoing wearable device 100 or another electronic device. The electronic device includes a processor, a memory, and a Bluetooth module. The processor, the memory, and the Bluetooth module (for example, a Bluetooth module) are coupled. The processor is provided with at least two MAC addresses. The at least two MAC addresses include a first MAC address and a second MAC address. The memory is configured to store computer program code, and the computer program code includes computer instructions. The memory is further configured to store the at least two MAC addresses.

When the processor executes the computer instructions, the electronic device performs the following operation: the processor controls, in response to a third operation of a user, the Bluetooth module to use a first MAC address; and controls, in response to a fourth operation of the user, the Bluetooth module to use a second MAC address.

In some embodiments, the electronic device may further include a preset switch (namely, the foregoing second preset hardware switch or key). The third operation and the fourth operation may be different operations performed by the user on the preset switch.

In some embodiments, the electronic device further includes a display. The processor is further configured to control the display to display a Bluetooth setting interface in response to a fifth operation of the user. The Bluetooth setting interface includes an option corresponding to the first MAC address and an option corresponding to the second MAC address. The third operation is a selection operation performed by the user on the option corresponding to the first MAC address in the Bluetooth setting interface, and the fourth operation is a selection operation performed by the user on the option corresponding to the second MAC address in the Bluetooth setting interface.

An embodiment of this application further provides a computer storage medium. The computer storage medium includes computer instructions. When the computer instructions are run on the foregoing electronic device, the electronic device is enabled to perform functions performed by the electronic device in the description of the foregoing embodiments.

An embodiment of this application further provides a computer program product. When the computer program product runs on a computer, the computer is enabled to perform functions performed by the electronic device in the description of the foregoing embodiments.

The foregoing descriptions about implementations allow a person skilled in the art to understand that, for the purpose of convenient and brief description, division into the foregoing function modules is used as an example for illustration. In actual application, the foregoing functions can be allocated to different function modules and implemented according to a requirement, that is, an inner structure of an apparatus is divided into different function modules to implement all or some of the functions described above. For a detailed working process of the foregoing system, apparatus, and unit, refer to a corresponding process in the foregoing method embodiments, and details are not described herein again.

In the several embodiments provided in the embodiments of this application, it should be understood that the disclosed system, apparatus, and method may be implemented in other manners. For example, the described apparatus embodiment is merely an example. For example, division into the modules or units is merely logical function division and may be other division in actual implementation. For example, a plurality of units or components may be combined or integrated into another system, or some features may be ignored or not performed. In addition, the displayed or discussed mutual couplings or direct couplings or communication connections may be implemented by using some interfaces. The indirect couplings or communication connections between the apparatuses or units may be implemented in electronic, mechanical, or other forms.

The units described as separate parts may or may not be physically separate, and parts displayed as units may or may not be physical units, may be located in one position, or may be distributed on a plurality of network units. Some or all of the units may be selected based on actual requirements to achieve the objectives of the solutions of the embodiments.

In addition, functional units in the embodiments of this application may be integrated into one processing unit, or each of the units may exist alone physically, or two or more units are integrated into one unit. The integrated unit may be implemented in a form of hardware, or may be implemented in a form of a software functional unit.

When the integrated unit is implemented in the form of a software functional unit and sold or used as an independent product, the integrated unit may be stored in a computer-readable storage medium. Based on such an understanding, the technical solutions in the embodiments, or the part contributing to the conventional technology, or all or some of the technical solutions may be implemented in the form of a software product. The computer software product is stored in a storage medium and includes several instructions for instructing a computer device (which may be a personal computer, a server, or a network device) or a processor to perform all or some of the steps of the methods described in the embodiments. The foregoing storage medium includes, any medium that can store program code, such as a flash memory, a removable hard disk, a read-only memory, a random access memory, a magnetic disk, or an optical disc.

The foregoing descriptions are merely specific implementations of the embodiments, but are not intended to limit the protection scope of the embodiments. Any variation or replacement within the technical scope disclosed in the embodiments shall fall within the protection scope of the embodiments. Therefore, the protection scope of the embodiments shall be subject to the protection scope of the claims.

What is claimed is:

1. A method comprising:
   receiving, from a user, a first user operation, wherein the first user operation is fastening a device body of a wearable device to a first carrier of the wearable device, and wherein the wearable device comprises a first working mode and a second working mode;
   starting, in response to the first user operation, the first working mode to collect first activity data, wherein the first activity data is daily activity data of the user;
   receiving, from the user, a second user operation, wherein the second user operation is fastening the device body to a second carrier;
   starting, in response to the second user operation, the second working mode to collect second activity data, wherein the second activity data is professional exercise data of the user; and
   detecting a contact voltage of a detection port of a switching circuit of the device body, wherein the switching circuit comprises a detection contact and the detection port,
   wherein in response to the first user operation and when the detection contact is in contact with a first metal contact of the first carrier:
      detecting that the contact voltage is a first voltage value; and
      starting, in response to detecting that the contact voltage is the first voltage value, the first working mode to collect the first activity data, and
   wherein in response to the second user operation and when the detection contact is in contact with a second metal contact of the second carrier:
      detecting that the contact voltage is a second voltage value; and
      starting, in response to detecting that the contact voltage is the second voltage value, the second working mode to collect the second activity data.

2. The method of claim 1, further comprising:
   identifying that the wearable device is in the first working mode when the device body is fastened to the first carrier; and
   identifying that the wearable device is in the second working mode when the device body is fastened to the second carrier of the wearable device.

3. The method of claim 1, further comprising:
   starting, in response to the first user operation, a first-type sensor of the wearable device to enable the wearable device to work in the first working mode, wherein the first-type sensor is located in the device body and is configured to collect the first activity data; and
   starting, in response to the second user operation, a second-type sensor of the wearable device to enable the wearable device to work in the second working mode, wherein the second-type sensor is located in the device body and is configured to collect the second activity data, and wherein the first-type sensor is different than the second-type sensor.

4. The method of claim 1, wherein the first activity data comprises one or more of a quantity of steps, a heart rate, or a sleep parameter of the user, and wherein:
   the second activity data comprises one or more of a touch-ground time, a touch-ground impact, a leg swing angle, or a valgus amplitude generated when the user is running and when the second working mode is a running mode; and
   the second activity data comprises one or more of a running distance, a quantity of jumps, or a jump height when the second working mode is a basketball mode.

5. The of claim 2, wherein the first user operation and the second user operation are different user operations received from the user either:
   on a first preset hardware switch or key of the device body; or
   on a first preset button or option displayed on a display of the device body.

6. The method of claim 1, wherein after starting the first working mode to collect the first activity data, the method further comprises:
   presenting the first activity data to the user; or
   sending the first activity data to an electronic device using a wireless connection to the electronic device to enable the electronic device to present the first activity data to the user.

7. The method of claim 1, wherein after starting the second working mode to collect the second activity data, the method further comprises:
presenting the second activity data to the user; or
sending the second activity data to an electronic device using a wireless connection to the electronic device to enable the electronic device to present the second activity data to the user.

8. A wearable device comprising:
a device body;
a switching circuit comprising a detection contact and a detection port;
a first carrier coupled to the device body and comprising a first metal contact;
a second carrier coupled to the device body and comprising a second metal contact;
a memory configured to store computer instructions; and
a processor coupled to the device body and the memory and comprising a first working mode and a second working mode, wherein the processor is configured to execute the computer instructions to cause the wearable device to be configured to:
receive, from a user, a first user operation, wherein the first user operation is fastening the device body to the first carrier;
start, in response to the first user operation, the first working mode to collect first activity data, wherein the first activity data is daily activity data of the user;
receive, from the user, a second user operation, wherein the second user operation is fastening the device body to the second carrier;
start, in response to the second user operation, the second working mode to collect second activity data, wherein the second activity data is professional exercise data of the user; and
detect a contact voltage of the detection port,
wherein in response to the first user operation and when the detection contact is in contact with the first metal contact:
detect that the contact voltage is a first voltage value; and
start, in response to detecting that the contact voltage is the first voltage value, the first working mode to collect the first activity data, and
wherein in response to the second user operation and when the detection contact is in contact with the second metal contact:
detect that the contact voltage is a second voltage value; and
start, in response to detecting that the contact voltage is the second voltage value, the second working mode to collect the second activity data.

9. The wearable device of claim 8, wherein the processor is comprised in the device body, wherein both the first carrier and the second carrier are configured to fasten the device body, wherein the device body is configured to be worn on a body, a shoe, a suit, or an accessory of the user using the first carrier or the second carrier, and wherein the processor is further configured to execute the computer instructions to cause the wearable device to:
identify that the wearable device is in the first working mode when the device body is fastened to the first carrier; and
identify that the wearable device is in the second working mode when the device body is fastened to the second carrier.

10. The wearable device of claim 8, wherein the device body comprises a first-type sensor and a second-type sensor, and wherein the processor is further configured to execute the computer instructions to cause the wearable device to:
start, in response to the first user operation, the first-type sensor to enable the wearable device to work in the first working mode, wherein the first-type sensor is configured to collect the first activity data; and
start, in response to the second user operation, the second-type sensor to enable the wearable device to work in the second working mode, wherein the second-type sensor is configured to collect the second activity data, and wherein the first-type sensor is different than the second-type sensor.

11. The wearable device of claim 8, wherein the first activity data comprises one or more types of a quantity of steps, a heart rate, or a sleep parameter of the user, and wherein:
the second activity data comprises one or more types of a touch-ground time, a touch-ground impact, a leg swing angle, or a valgus amplitude generated when the user is running and when the second working mode is a running mode; and
the second activity data comprises one or more types of a running distance, a quantity of jumps, or a jump height when the second working mode is a basketball mode.

12. The wearable device of claim 9, wherein either the device body further comprises a first preset hardware switch or key, or a display, and wherein the first user operation and the second user operation are different user operations received from the user either:
on the first preset hardware switch or key; or
on a first preset button or option displayed on the display.

13. The wearable device of claim 8, wherein the processor is further configured to execute the computer instructions to cause the wearable device to:
present the first activity data to the user after starting the first working mode, or
wherein the device body comprises a wireless communications component that is configured to:
establish a wireless connection to an electronic device; and
send the first activity data to the electronic device through the wireless connection to enable the electronic device to present the first activity data to the user.

14. A computer program product comprising computer-executable instructions stored on a non-transitory computer storage medium that, when executed by a processor, cause a wearable device to:
receive, from a user, a first user operation, wherein the first user operation is fastening a device body of the wearable device to a first carrier of the wearable device;
start, in response to the first user operation, a first working mode to collect first activity data, wherein the first activity data is daily activity data of the user;
receive, from the user, a second user operation, wherein the second user operation is fastening the device body to a second carrier;
start, in response to the second user operation, a second working mode to collect second activity data, wherein the second activity data is professional exercise data of the user; and
detect a contact voltage of a detection port of a switching circuit of the device body, wherein the switching circuit comprises a detection contact and the detection port, wherein in response to the first user operation and when the detection contact is in contact with a first metal contact of the first carrier:
  detect that the contact voltage is a first voltage value; and
  start, in response to detecting that the contact voltage is the first voltage value, the first working mode to collect the first activity data, and
wherein in response to the second user operation and when the detection contact is in contact with a second metal contact of the second carrier:
  detect that the contact voltage is a second voltage value; and
  start, in response to detecting that the contact voltage is the second voltage value, the second working mode to collect the second activity data.

15. The computer program product of claim 14, wherein the first activity data comprises one or more of a quantity of steps, a heart rate, or a sleep parameter of the user, and wherein:
  the second activity data comprises one or more of a touch-ground time, a touch-ground impact, a leg swing angle, or a valgus amplitude generated when the user is running and when the second working mode is a running mode; and
  the second activity data comprises one or more of a running distance, a quantity of jumps, or a jump height when the second working mode is a basketball mode.

16. The computer program product of claim 14, wherein the first user operation and the second user operation are different user operations received from the user on a first preset hardware switch or key of the device body.

17. The computer program product of claim 14, wherein the first user operation and the second user operation are different user operations received from the user on a first preset button or option displayed on a display of the device body.

18. The computer program product of claim 14, wherein after starting the first working mode to collect the first activity data, the computer-executable instructions that, when executed by the processor, cause the wearable device to present the first activity data to the user.

19. The computer program product of claim 14, wherein after starting the first working mode to collect the first activity data, the computer-executable instructions that, when executed by the processor, cause the wearable device to send the first activity data to an electronic device using a wireless connection to the electronic device to enable the electronic device to present the first activity data to the user.

20. The computer program product of claim 14, wherein after starting the second working mode to collect the second activity data, the computer-executable instructions that, when executed by the processor, cause the wearable device to:
  present the second activity data to the user; or
  send the second activity data to an electronic device using a wireless connection to the electronic device to enable the electronic device to present the second activity data to the user.

* * * * *